US010973478B2

(12) United States Patent
Gregerson et al.

(10) Patent No.: US 10,973,478 B2
(45) Date of Patent: Apr. 13, 2021

(54) CANTILEVERED X-RAY CT SYSTEM FOR MULTI-AXIS IMAGING

(71) Applicant: Mobius Imaging LLC, Shirley, MA (US)

(72) Inventors: Eugene A. Gregerson, Bolton, MA (US); Russell Stanton, Luchenberg, MA (US); Michael Connor, Dunstable, MA (US); Paul Sebring, Townsend, MA (US)

(73) Assignee: Mobius Imaging LLC, Shirley, MA (US)

( * ) Notice: Subject to any disclaimer, the term of this patent is extended or adjusted under 35 U.S.C. 154(b) by 0 days.

(21) Appl. No.: 16/818,060

(22) Filed: Mar. 13, 2020

(65) Prior Publication Data

US 2020/0268332 A1 Aug. 27, 2020

Related U.S. Application Data

(63) Continuation of application No. 15/817,672, filed on Nov. 20, 2017, now Pat. No. 10,624,596.

(Continued)

(51) Int. Cl.
*A61B 6/00* (2006.01)
*A61B 6/04* (2006.01)
(Continued)

(52) U.S. Cl.
CPC .............. *A61B 6/4476* (2013.01); *A61B 6/00* (2013.01); *A61B 6/03* (2013.01); *A61B 6/035* (2013.01);
(Continued)

(58) Field of Classification Search
None
See application file for complete search history.

(56) References Cited

U.S. PATENT DOCUMENTS 4,961,208 A 10/1990 Okada
5,448,607 A 9/1995 McKenna
(Continued)

FOREIGN PATENT DOCUMENTS

DE 19846980 A1 10/1999
EP 0067933 A1 12/1982
(Continued)

OTHER PUBLICATIONS

Ergun, "Equina.TM.: A CT Scanner Designed by and for Veterinarians", Asto CT, 12 pages, (Nov. 24, 2016).
(Continued)

*Primary Examiner* — Hoon K Song
(74) *Attorney, Agent, or Firm* — Howard & Howard Attorneys PLLC

(57) ABSTRACT

A multi-axis imaging system comprising an imaging gantry with an imaging axis extending through a bore of the imaging gantry, a support column that supports the imaging gantry on one side of the gantry in a cantilevered manner, and a base that supports the imaging gantry and the support column. The imaging system including a first drive mechanism that translates the gantry in a vertical direction relative to the support column and the base, a second drive mechanism that rotates the gantry with respect to the support column between a first orientation where the imaging axis of the imaging gantry extends in a vertical direction parallel to the support column and a second orientation where the imaging axis of the gantry extends in a horizontal direction parallel with the base, and a third drive mechanism that translates the support column and the gantry in a horizontal direction along the base.

18 Claims, 25 Drawing Sheets

Related U.S. Application Data

(60) Provisional application No. 62/425,746, filed on Nov. 23, 2016.

(51) Int. Cl.

| | |
|---|---|
| *A61B 6/03* | (2006.01) |
| *B25J 19/00* | (2006.01) |
| *A61B 5/055* | (2006.01) |
| *B25J 15/00* | (2006.01) |
| *B25J 5/02* | (2006.01) |
| *B25J 9/10* | (2006.01) |
| *B25J 9/16* | (2006.01) |
| *B25J 9/00* | (2006.01) |

(52) U.S. Cl.
CPC .......... *A61B 6/0407* (2013.01); *A61B 6/4447* (2013.01); *A61B 6/4458* (2013.01); *A61B 6/504* (2013.01); *A61B 6/505* (2013.01); *A61B 6/508* (2013.01); *A61B 5/0555* (2013.01); *A61B 6/037* (2013.01); *B25J 5/02* (2013.01); *B25J 9/0096* (2013.01); *B25J 9/104* (2013.01); *B25J 9/1676* (2013.01); *B25J 15/0019* (2013.01); *B25J 19/0075* (2013.01)

(56) References Cited

U.S. PATENT DOCUMENTS

| | | | |
|---|---|---|---|
| 5,574,763 A | 11/1996 | Dehner | |
| 5,574,769 A | 11/1996 | Dehner | |
| 6,102,567 A | 8/2000 | Cabral et al. | |
| 6,246,239 B1 | 6/2001 | Krogmann et al. | |
| 6,735,274 B1 | 5/2004 | Zahavi et al. | |
| 6,794,871 B2 | 9/2004 | Imai et al. | |
| 7,224,764 B2 | 5/2007 | Sukovic et al. | |
| 7,456,407 B2 | 11/2008 | Stark | |
| 7,607,832 B2 | 10/2009 | Jensen et al. | |
| 7,796,730 B2 * | 9/2010 | Marash ................ | A61B 6/0421 378/65 |
| 7,806,589 B2 | 10/2010 | Tashman et al. | |
| 7,944,208 B2 | 5/2011 | Dutto et al. | |
| 8,118,488 B2 | 2/2012 | Gregerson | |
| 9,301,726 B2 | 4/2016 | Mackie et al. | |
| 10,624,596 B2 | 4/2020 | Gregerson et al. | |
| 2004/0170254 A1 | 9/2004 | Gregerson et al. | |
| 2005/0053186 A1 | 3/2005 | Sukovic et al. | |
| 2008/0123819 A1 | 5/2008 | Jensen et al. | |
| 2008/0224051 A1 | 9/2008 | Conwell | |
| 2009/0289663 A1 | 11/2009 | Sogomonyan et al. | |
| 2010/0172468 A1 | 7/2010 | Gregerson | |
| 2011/0200175 A1 * | 8/2011 | Gregerson ........... | A61B 6/4447 378/197 |
| 2011/0222667 A1 * | 9/2011 | Gregerson ........... | A61B 6/4429 378/198 |
| 2011/0228901 A1 | 9/2011 | Yorkston et al. | |
| 2011/0228910 A1 | 9/2011 | Gregerson et al. | |
| 2012/0256099 A1 | 10/2012 | Gregerson | |
| 2012/0324648 A1 | 12/2012 | Amano | |
| 2013/0343509 A1 | 12/2013 | Gregerson et al. | |
| 2014/0139215 A1 * | 5/2014 | Gregerson ........... | A61B 6/4447 324/309 |
| 2015/0313557 A1 | 11/2015 | Mackie et al. | |
| 2016/0128653 A1 | 5/2016 | Fortuna et al. | |
| 2018/0028127 A1 * | 2/2018 | Litzenberger .......... | A61B 6/035 |
| 2018/0055707 A1 | 3/2018 | Stanton | |
| 2018/0177473 A1 | 6/2018 | Gregerson et al. | |

FOREIGN PATENT DOCUMENTS

| | | |
|---|---|---|
| EP | 0495137 A1 | 7/1992 |
| JP | H02123211 U | 10/1990 |
| JP | H04352948 A | 12/1992 |
| JP | 2000214263 A | 8/2000 |
| JP | 2000312674 A | 11/2000 |
| JP | 200137747 A | 2/2001 |
| JP | 2008278902 A | 11/2008 |
| WO | 2007141221 A1 | 12/2007 |
| WO | 2011111119 A1 | 9/2011 |
| WO | 2011135191 A1 | 11/2011 |

OTHER PUBLICATIONS

Ergun, et al., Preventing equine fractures with safe, high-quality CT imaging: The Asto CT Equina.TM., White Paper, www.astoct.com, 2 pages.

First Office Action from the European Patent Office in Application No. 13 804 681.8-1124 based on related Application No. PCT/US2013/045563, dated Jan. 9, 2018.

International Preliminary Report on Patentability (Chapter 1 of the Patent Cooperation Treaty) and Written Opinion of the International Search Authority in related International Application No. PCT/US2017/062776 dated Jun. 6, 2019.

International Preliminary Report on Patentability (Chapter 1 of the Patent Cooperation Treaty) in International Application No. PCT/US2013/045563 dated Dec. 24, 2014.

International Search Report and Written Opinion issued in PCT Application No. PCT/US2013/045563 dated Sep. 16, 2013.

Notification of Transmittal of the International Search Report and the Written Opinion of the International Searching Authority in related application No. PCT/US2017/062776 dated Feb. 13, 2018.

Supplementary European Search Report from the Munich Patent Office for Application No. 13804681.8-1660/2861148 in International Application No. PCT/US2013/045563 dated Dec. 17, 2015.

* cited by examiner

SECTION B-B

DETAIL C

DETAIL D

CANTILEVERED X-RAY CT SYSTEM FOR MULTI-AXIS IMAGING

CROSS-REFERENCE TO RELATED APPLICATIONS

This Application is a Continuation of application Ser. No. 15/817,672 filed on Nov. 20, 2017. Application Ser. No. 15/817,672 claims the benefit of U.S. Provisional Application 62/425,746 filed on Nov. 23, 2016.

BACKGROUND

Conventional medical imaging devices, such as x-ray computed tomography (CT) imaging devices, are limited in the types of imaging operations that may be performed.

SUMMARY

Embodiments include a multi-axis imaging system and methods for imaging a human or animal using a multi-axis imaging system. The various embodiments include a multi-axis imaging system that includes an imaging gantry, a support column that supports the imaging gantry on one side of the gantry in a cantilevered manner, a base that supports the imaging gantry and the support column, a first drive mechanism that translates the gantry in a vertical direction relative to the support column, a second drive mechanism that rotates the gantry with respect to the support column, and a third drive mechanism that translates the support column and the gantry in a horizontal direction relative to the base.

Further embodiments include a method of operating a multi-axis imaging system comprising a moveable imaging gantry, the method including receiving, from a control system of a moveable patient support, data indicating the configuration of the patient support, and sending control signals to one or more drive systems of the multi-axis imaging system to cause the gantry to translate and/or rotate to maintain the gantry spaced away from the patient support and a bore of the gantry aligned with the patient support in response to the data received from the control system of the moveable patient support.

Further embodiments include a control system for a multi-axis imaging system having a moveable imaging gantry and a movable patient support, the control system including a memory and a processor configured with processor-executable instructions to perform operations including receiving data indicating a configuration of the movable patient support, and sending control signals to one or more drive systems of the multi-axis imaging system to cause the gantry to translate and/or rotate to maintain the gantry spaced away from the patient support and a bore of the gantry aligned with the patient support in response to the data received from the control system of the moveable patient support.

Further embodiments include a multi-axis imaging system for imaging an animal in a weight-bearing position that includes a gantry, a support column that supports the gantry, and a support stage on which an animal stands, wherein the gantry is translatable with respect to the support stage in a vertical direction to scan one or more legs of the animal standing on the support stage and the gantry is translatable in a vertical and in a horizontal direction with respect to the support stage to scan a head and/or neck of the animal standing on the support stage.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1:
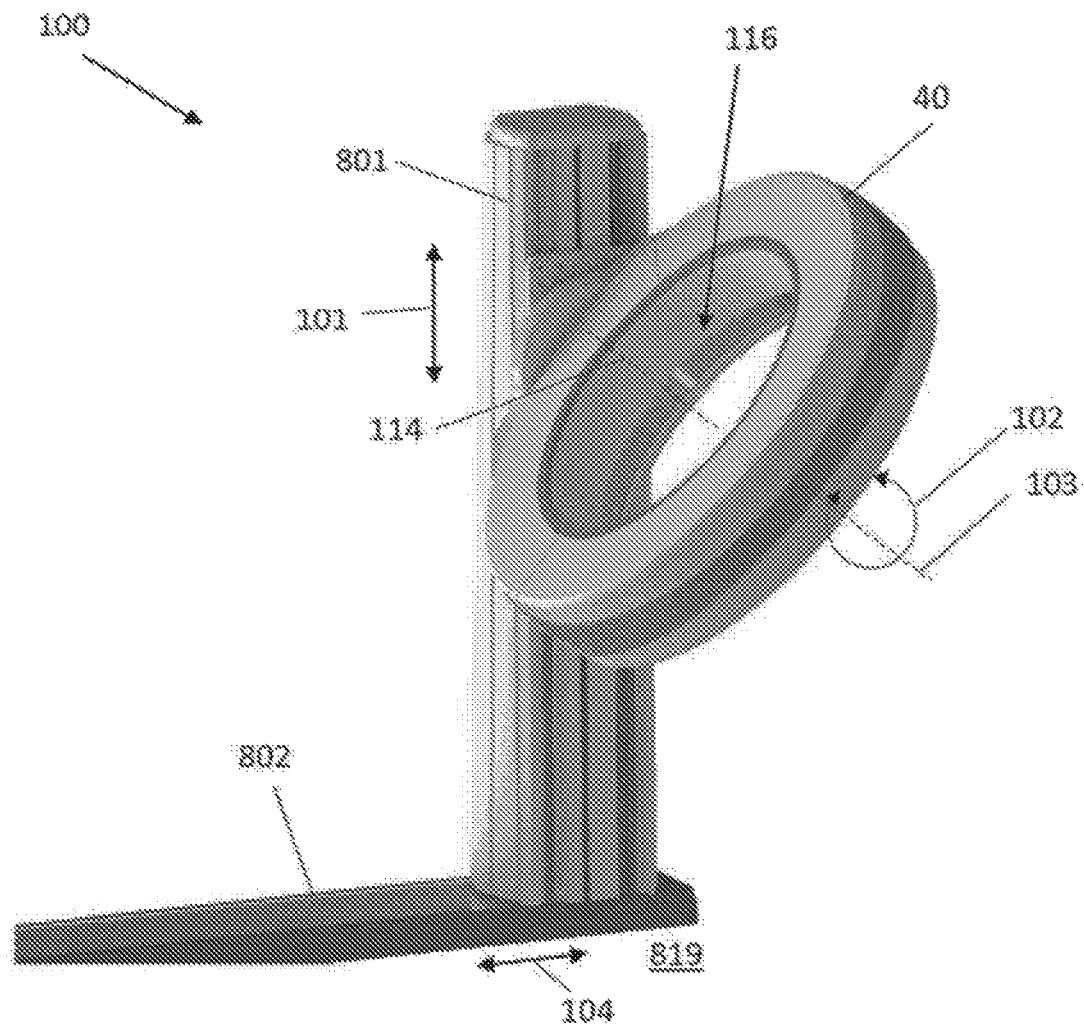
FIG. 1 illustrates a multi-axis ct imaging device according to an embodiment.

Referring to FIG. 1, an imaging system 100 according to one embodiment of the invention is shown. The system 100 includes image collection components, such as a rotating x-ray source and detector array, a rotating gamma-ray camera or stationary magnetic resonance imaging components, that are housed within the gantry 40. The system 100 is configured to collect imaging data, such as, for example x-ray computed tomography (CT), positron emission tomography (PET), single-photon emission computed tomography (SPECT) or magnetic resonance imaging (MRI) data, from an object located within the bore 116 of the gantry 40, in any manner known in the medical imaging field. In embodiments, the system 100 may be an x-ray CT imaging system, and may include an x-ray source and a detector located within the gantry 40. The gantry 40 may also include other components, such as a high-voltage generator, a heat exchanger, a power supply (e.g., battery system), and a computer. These components may be mounted on a rotating element (e.g., a rotor) that rotates within the gantry 40 during an imaging scan. A rotor drive mechanism may also be located on the rotor, and may drive the rotation of the rotor. Between scans, a docking system may be used to couple the rotating and non-rotating portions of the system 100 for power and data communication.

The gantry 40 may be mounted to a support column 801. The support column 801 may be attached to the gantry 40 on a first side of the gantry 40 and may support the gantry 40 in a cantilevered manner. The gantry 40 may be a generally O-shaped structure having a central imaging bore 116 and defining an imaging axis 114 extending through the bore. The system 800 may also include a base 802 that may be located on a weight-bearing surface, such as a floor 819 of a building. In the illustrated embodiment, the base 802 comprises a generally rectilinear support structure that may be mounted (e.g., bolted) to the floor 819. The support column 801 may be located on and supported by the base 801 and may extend upwards from the top surface of the base 801 in a generally vertical direction. The support column 801 may have a length dimension that extends vertically at least about 2 meters, such as 2-5 meters (e.g., about 3 meters).

In various embodiments discussed in further detail below, the system 100 may enable imaging (e.g., CT scanning) in multiple orientations and along multiple directions. In embodiments, the system 100 may include a first drive mechanism for translating the gantry 40 relative to the support column 801 in a first direction along the direction of arrow 101 in FIG. 1. The first direction 101 may be a generally vertical direction (i.e., perpendicular to the floor 819), which for the purposes of this disclosure may be defined as ±15° from true vertical. The system 100 may also include a second drive mechanism for rotating the gantry 40 relative to the support column 801 in the direction indicated by arrow 102. The rotation of the gantry 40 may be with respect to an axis 103 that extends orthogonal to the first direction 101 and may be generally parallel to the floor 819. The axis 103 may extend through the isocenter of the bore 116 of the gantry 40. The system may also include a third drive mechanism for translating the gantry 40 and support column 801 with respect to the base 802 in a second direction indicated by arrow 104 in FIG. 1. The second direction 104 may be a generally horizontal direction (i.e., parallel to the floor 819), which for the purposes of this disclosure may be defined as ±15° from true horizontal. The second direction 104 may be orthogonal to both the first direction 101 and to the rotation axis 103.

Figure 2A:
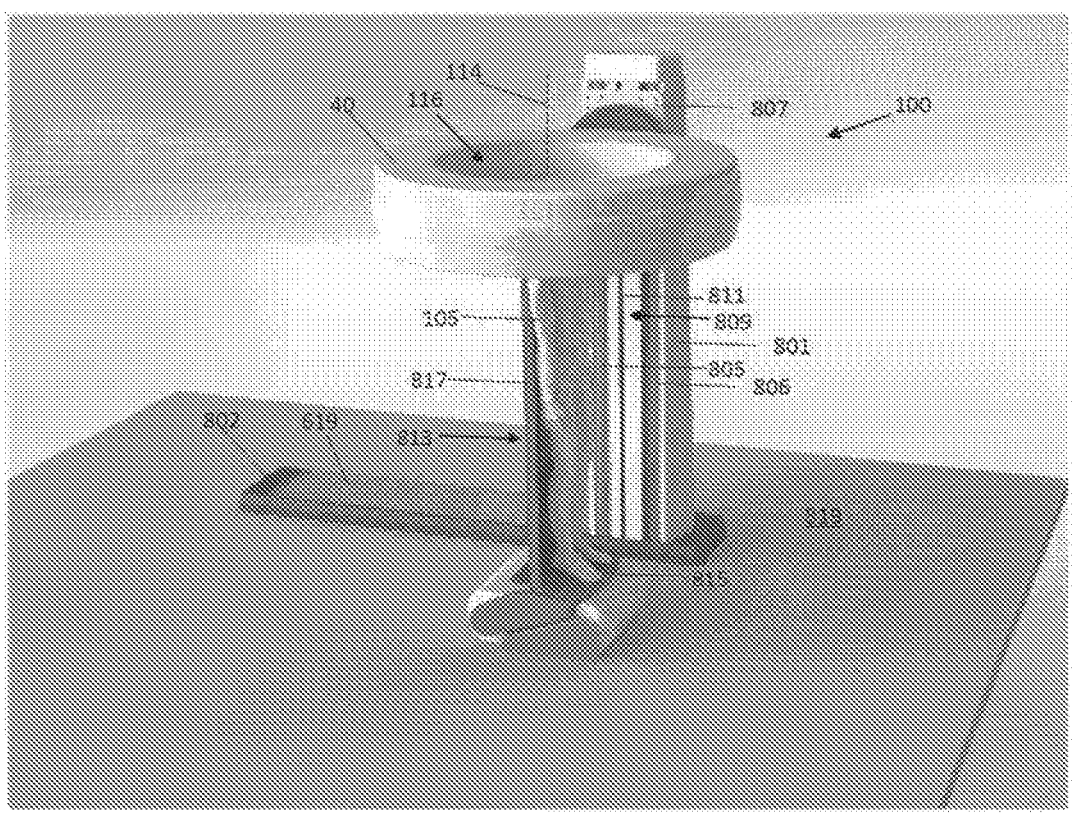
FIGS. 2A-2C illustrate a multi-axis x-ray CT imaging device performing a scan of a patient in a vertical direction.
Figure 2B:
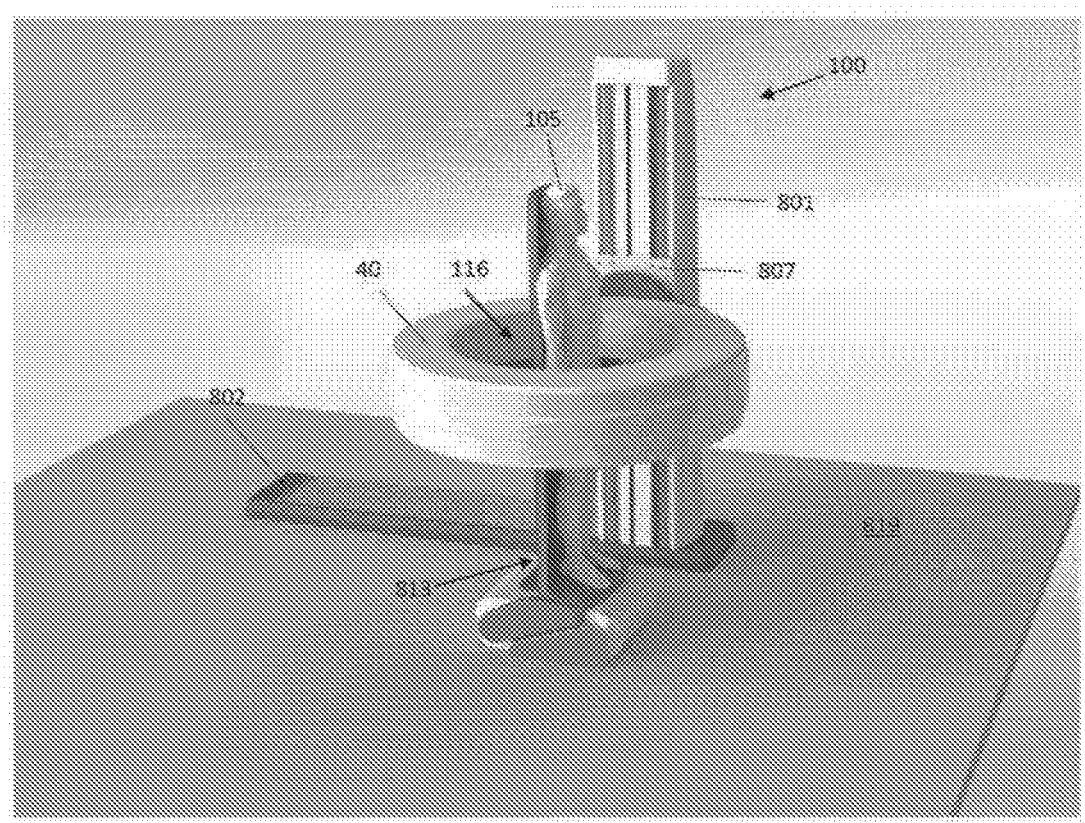
Figure 2C:
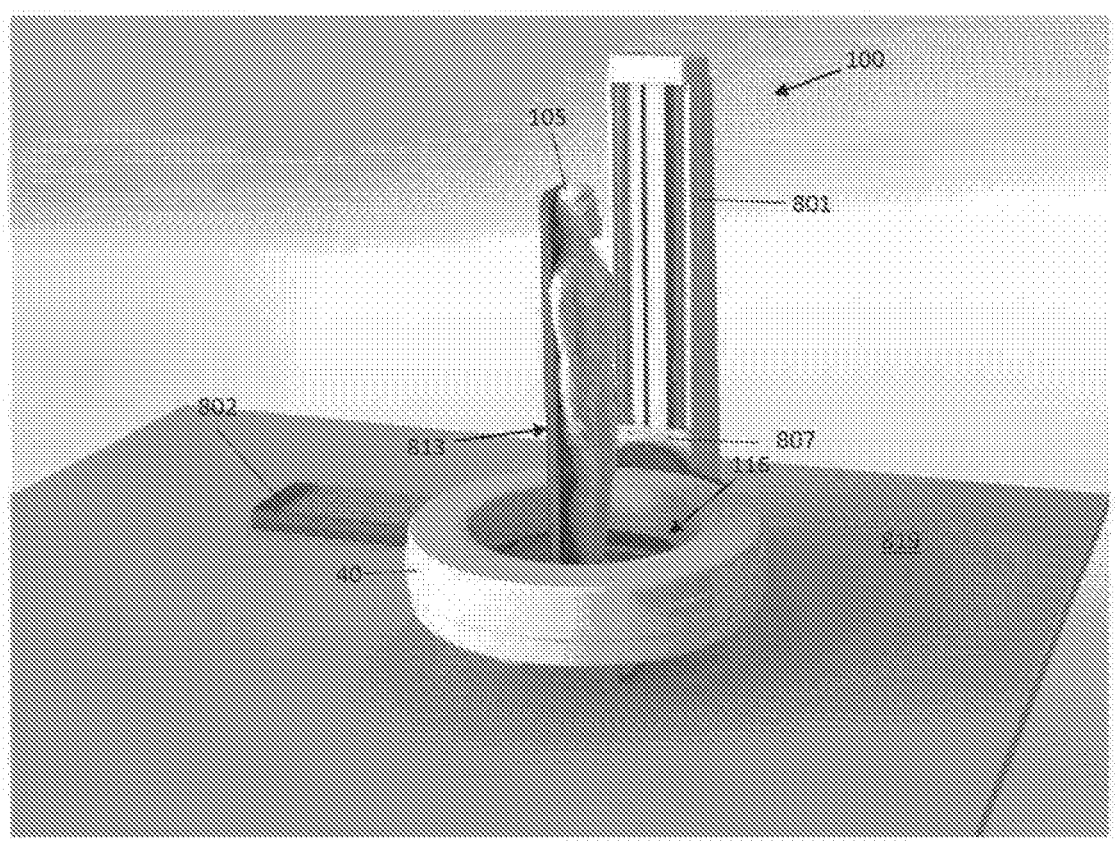

FIGS. 2A-2C, 3A-3C and 4A-4C illustrate an imaging system 100 in various configurations for performing imaging scans along multiple axes. In FIGS. 2A-2C, the support column 801 may support the gantry 40 in a generally vertical orientation, such that the front and rear faces of the gantry 40 extend parallel to the floor 819 and the imaging axis 114 through the gantry bore 116 extends in a vertical direction (i.e., perpendicular to the floor). The imaging axis 114 of the gantry 40 in this configuration may extend parallel to the length dimension of the vertically-extending support column 801.

The gantry 40 may be displaced along the length of the support column 801 in a generally vertical direction. This is illustrated in FIGS. 2A-2C, which show the gantry 40 displaced vertically from a first position in FIG. 2A with the gantry 40 located proximate a first end of the support column 801 (i.e., opposite the base 802), to a second position in FIG. 2B with the gantry 40 located approximately mid-way along the length of the support column 801, to a third position in FIG. 2C, with the gantry 40 located proximate to a second end of the support column 801 proximate to the base 802. The gantry 40 and the support column 801 may include mating features that confine the displacement of the gantry 40 along the length of the support column 801. As shown in FIGS. 2A-2C, for example, a pair of parallel rails 805, 806 may extend in a vertical direction along the length of the support column 801. A carriage 807 may be mounted to the side of the gantry 40 that attaches to the support column 801. The carriage 807 may include bearing elements (e.g., roller and/or dovetail bearing slides) that engage with the rails 805, 806 to provide linear motion of the carriage 807 and gantry 40 along the length of the support column 801.

A first drive mechanism may drive the displacement of the gantry 40 relative to the support column 801. An example of the first drive system 501 is described below with reference to FIGS. 5A-5D. A controller 810 (see FIG. 4A) may control the operation of the first drive mechanism 501 and thereby control the vertical displacement of the gantry 40. The controller may receive position feedback signals indicative of the position of the gantry 40 along the support column 801, such as from a linear encoder.

The system 100 may also include a patient support 813. The patient support 813 may support a patient 105 in a weight-bearing standing position as shown in FIGS. 2A-2C. The patient support 813 may include a first portion 815 that supports the feet of a patient upon which the patient 105 may stand. A second portion 817 may extend generally perpendicular to the first portion 815 and may provide additional support to the patient 105. For example, the patient 105 may lean against the second portion 817 during a scan and the second portion 817 may help to stabilize the patient 105 and prevent the patient 105 from falling off the patient support 813. In embodiments, the patient support 813 may support the patient 105 in a position that is raised above the floor 819, as shown in FIGS. 2A-2C. The first portion 815 and the second portion 817 may be made of a radiolucent (x-ray transparent) material, such as carbon fiber material.

The system 100 may be used to perform an imaging scan of a patient 105 in a weight-bearing standing position. For example, for an x-ray CT imaging system, the x-ray source and detector may rotate within the gantry 40 around the patient while the gantry 40 is displaced vertically on the support column 801 as shown in FIGS. 2A-2C to perform a helical scan of a patient 105 positioned on the patient support 813. In embodiments, the system 100 may scan over the full length of the patient (e.g., from the top of the patient's cranium to the bottom of the patient's feet) or any selected portion thereof. Following a scan, the gantry 40 may be moved to an out-of-the way position (e.g., to the top of the support column 801 or below the patient's feet) and the patient 105 may be removed from the patient support 813.

Figure 3A:
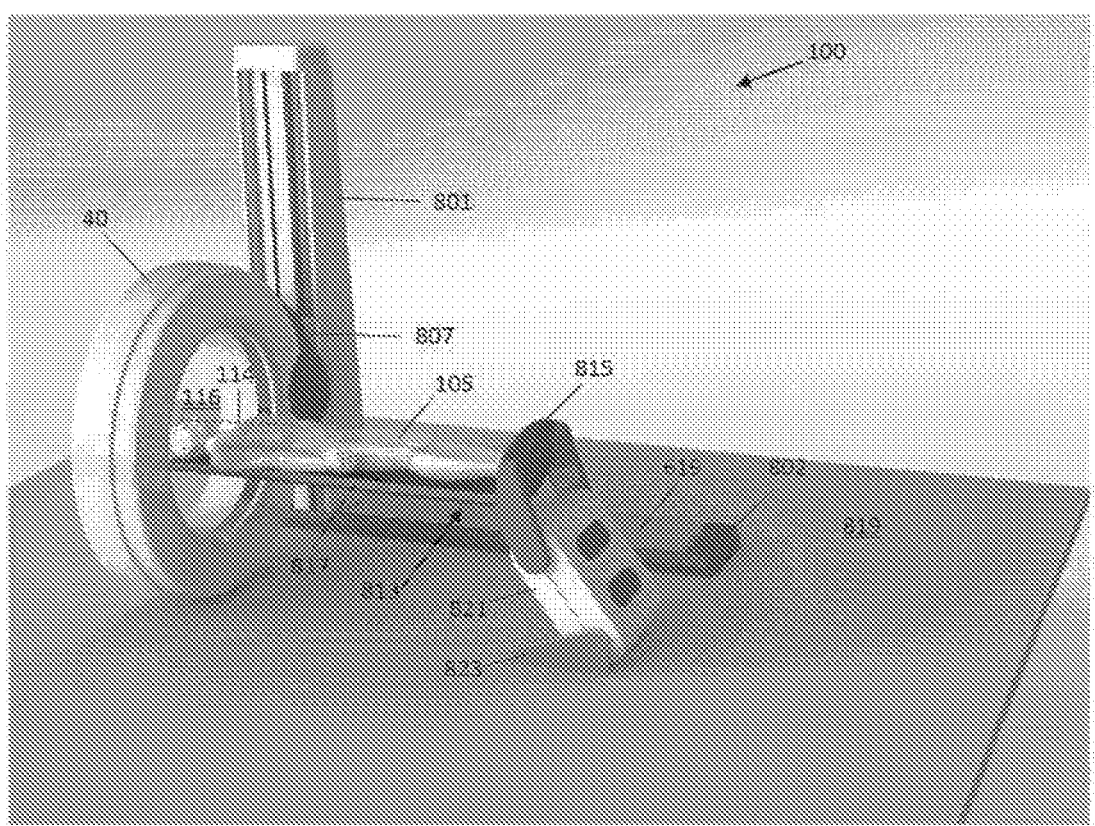
FIGS. 3A-3C illustrate the multi-axis x-ray CT imaging device performing a scan of a patient in a horizontal direction.
Figure 3B:
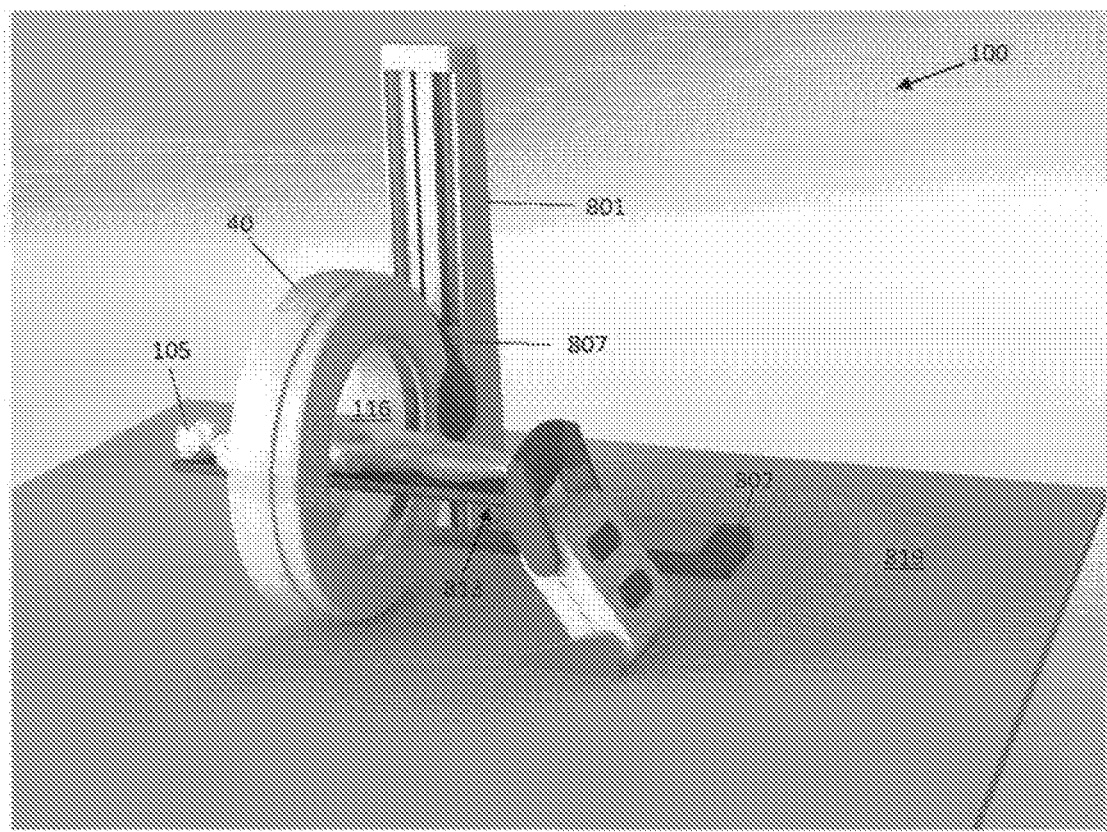
Figure 3C:
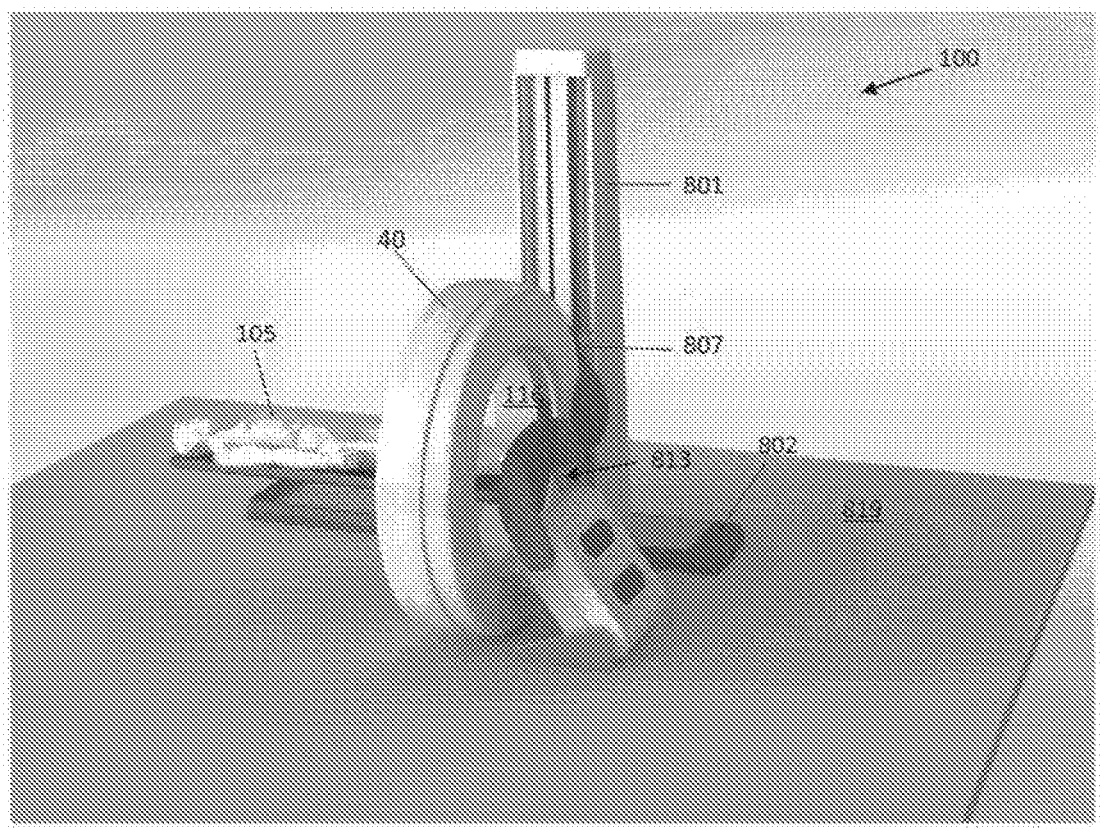

The gantry 40 may be attached to the support column 801 such that the gantry 40 may rotate (i.e., tilt) with respect to the support column 801. This is illustrated in FIGS. 3A-3C, which illustrate the gantry 40 tilted from a generally vertical orientation (as shown in FIGS. 2A-2C) with the front and rear faces of the gantry 40 extending parallel to the floor 819 and the imaging axis 114 extending in a vertical direction (i.e., perpendicular to the floor) to a generally horizontal orientation with the front and rear faces of the gantry extending perpendicular to the floor 819 and the imaging axis 114 extending in a horizontal direction (i.e., parallel to the floor). The imaging axis 114 of the gantry 40 in the configuration shown in FIGS. 2A-2C may extend perpendicular to the length dimension of the vertically-extending support column 801.

In embodiments, a rotary bearing may enable the rotation of the gantry 40 with respect to the support column 801. In one embodiment, the rotary bearing may include a first portion (i.e., bearing race) mounted to the carriage 807 and a second portion (i.e., bearing race) mounted to the gantry 40. The two bearing portions may rotate concentrically relative to one another such that the gantry 40 may be rotated relative to the carriage 807 and support column 801. In embodiments, the gantry 40 may rotate at least about 90° relative to the support column 801 (e.g., as is illustrated by FIGS. 2A-2C and FIGS. 3A-3C). In some embodiments, the gantry 40 may rotate at least about 180°, such as at least about 270°, including about 300° or more, relative to the support column 801.

A second drive mechanism may drive the rotation of the gantry 40 relative to the support column 801. An example of the second drive system 503 is described below with reference to FIGS. 5A-5D. The system controller 810 (see FIG. 4A) may control the operation of the second drive mechanism 503 and thereby control the rotational angle (tilt) of the gantry 40 relative to the support column 801. The controller may receive position feedback signals indicative of the rotational position of the gantry 40 with respect to the support column 801, such as from a rotary encoder.

In some embodiments, the patient support 813 may move from a first configuration as shown in FIGS. 2A-2C to a second configuration as shown in FIGS. 3A-3C. In the configuration of FIGS. 2A-2C, the first portion 815 of the patient support 813 may extend in a generally horizontal direction (i.e., parallel to the floor 819) and the second portion 817 may extend in a generally vertical direction (i.e., away from the floor 819). In the configuration of FIGS. 3A-3C, the second portion 817 of the patient support 813 may extend in a generally horizontal direction (i.e., parallel to the floor 819) and the first portion 815 may extend in a generally vertical direction. Put another way, the patient support 813 may tilt by a predetermined angle (e.g., ~90°) relative to the floor 819 between the configuration shown in FIGS. 2A-2C and the configuration shown in FIGS. 3A-3C. In embodiments, the table configuration of FIGS. 2A-2C may be used for scanning a patient in a weight-bearing standing position and the table configuration of FIGS. 3A-3C may be used for scanning a patient in a lying position, as in conventional x-ray CT systems.

In some embodiments, the patient support 813 may rotate (tilt) with respect to a linkage member 821 to which the patient support 813 is attached. In embodiments, the linkage member 821 may also rotate with respect to the floor 819. For example, the linkage member 821 may be attached to a base 823 that may be mounted to the floor 819. The linkage member 821 may rotate relative to the base 823. The rotation of the linkage member 821 relative to the base 823 may raise and lower the patient support 813 relative to the floor 819. A table control system may provide coordinated rotational motion of the patient support 813 relative to the linkage member 821 and rotational motion of the linkage member 821 relative to the base 823 to move the table system from the configuration shown in FIGS. 2A-2C to the configuration shown in FIGS. 3A-3C. An example of a patient table system that may be used with the system 100 is described in U.S. patent application Ser. No. 15/685,955 filed on Aug. 24, 2017, the entire contents of which were previously incorporated by reference herein.

FIGS. 3A-3C illustrate the system 100 performing an imaging scan of a patient 105 in a lying position. In particular, for an x-ray CT imaging system, the x-ray source and detector may rotate within the gantry 40 around the patient 105 while the gantry 40 is translated relative to the patient support 813 in a generally horizontal direction to perform a helical scan of a patient 105 lying on the patient support 813. In the embodiment shown in FIGS. 3A-3C, the gantry 40 and the support column 801 may translate relative to the patient 105 and patient support 813, which may be stationary during the scan. The gantry 40 and the support column 801 may translate along the length of the base 802. As shown in FIGS. 3A-3C, the gantry 40 may be displaced vertically on the support column 801 such that the patient 105 is aligned with the bore 116 of the gantry 40 and the imaging axis 114 extends along the length of the patient 105. The gantry 40 and the support column 801 may then translate along the base 802 in a horizontal direction from a first position as shown in FIG. 3A with the gantry 40 located over the head of the patient 105, to a second position as shown in FIG. 3B with the gantry 40 located over the mid-section of the patient 105, to a third position as shown in FIG. 3C with the gantry 40 located over the feet of the patient 105. The system 100 may perform a horizontal scan over the full length of the patient 105 or any selected portion thereof.

Figure 6A:
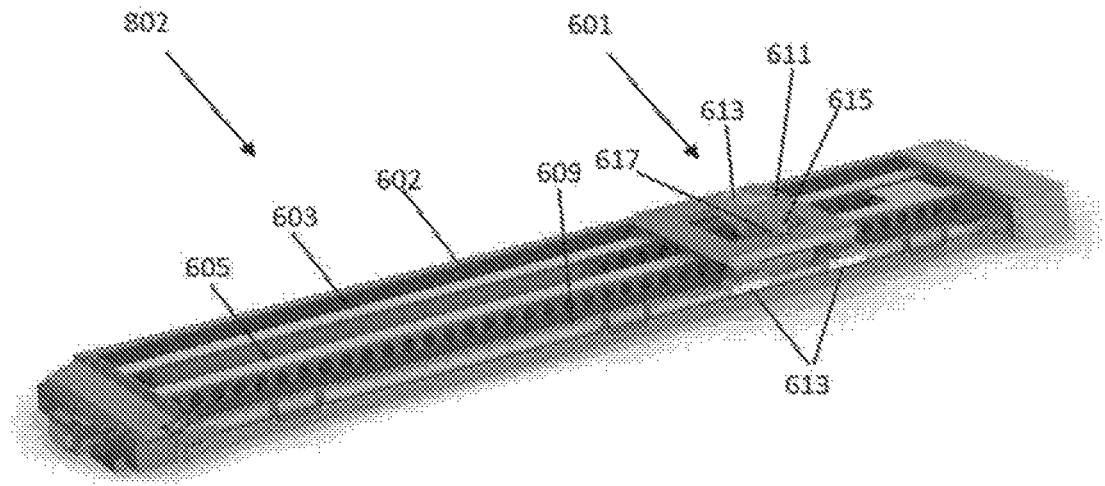
FIGS. 6A-6B illustrate a base of an x-ray CT imaging system according to an embodiment.
Figure 6B:
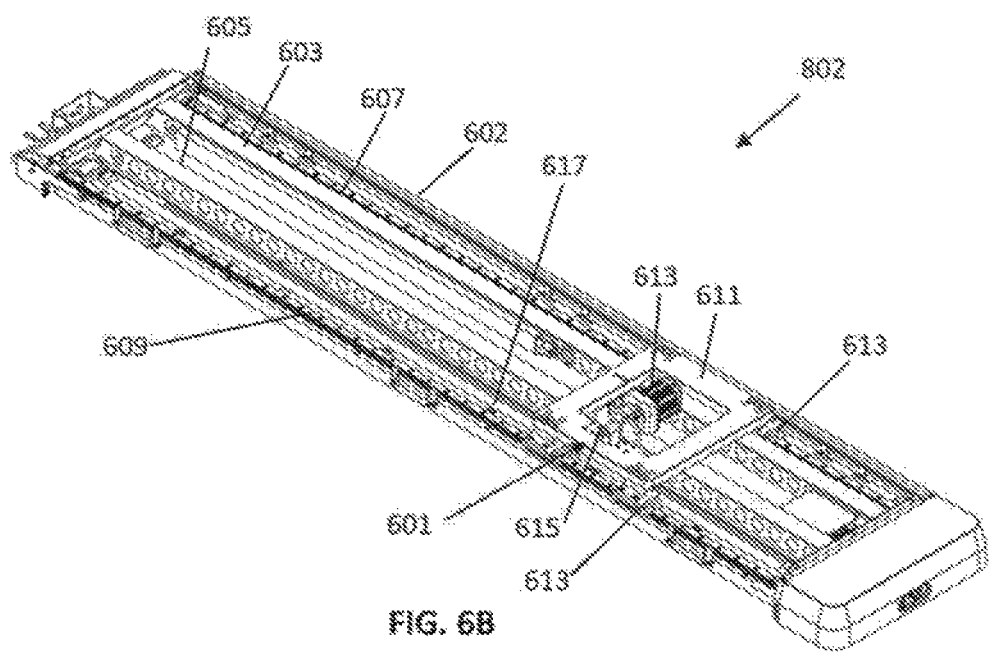

The base 802 and the support column 801 may include mating features that confine the translation of the support column in a horizontal direction along the length of the base 802. In the example of FIGS. 3A-3C, the base 802 may include rails or tracks that may mate with corresponding features at the bottom of the support column 801 to guide the translation of the support column 801 in a horizontal direction. A third drive mechanism may drive the translation of the support column 801 relative to the base 802. An example of a third drive mechanism 601 for translating the gantry 40 and support column 801 is schematically illustrated in FIGS. 6A-6B. The third drive mechanism 601 may comprise, for example, a belt drive, a drive wheel, a lead screw, a ball screw, a pulley, etc. or various combinations therefore. The third drive mechanism 601 may be mechanically coupled to and driven by one or more motors, which may be located in the support column 801 and/or the base 802. The system controller 810 (see FIG. 4A) may control the operation of the third drive mechanism 601 and thereby control the horizontal translation of the support column 801 and gantry 40. The controller 810 may receive position feedback signals indicative of the position of the support column 801 relative to the base 802, such as from a linear encoder.

Figure 4A:
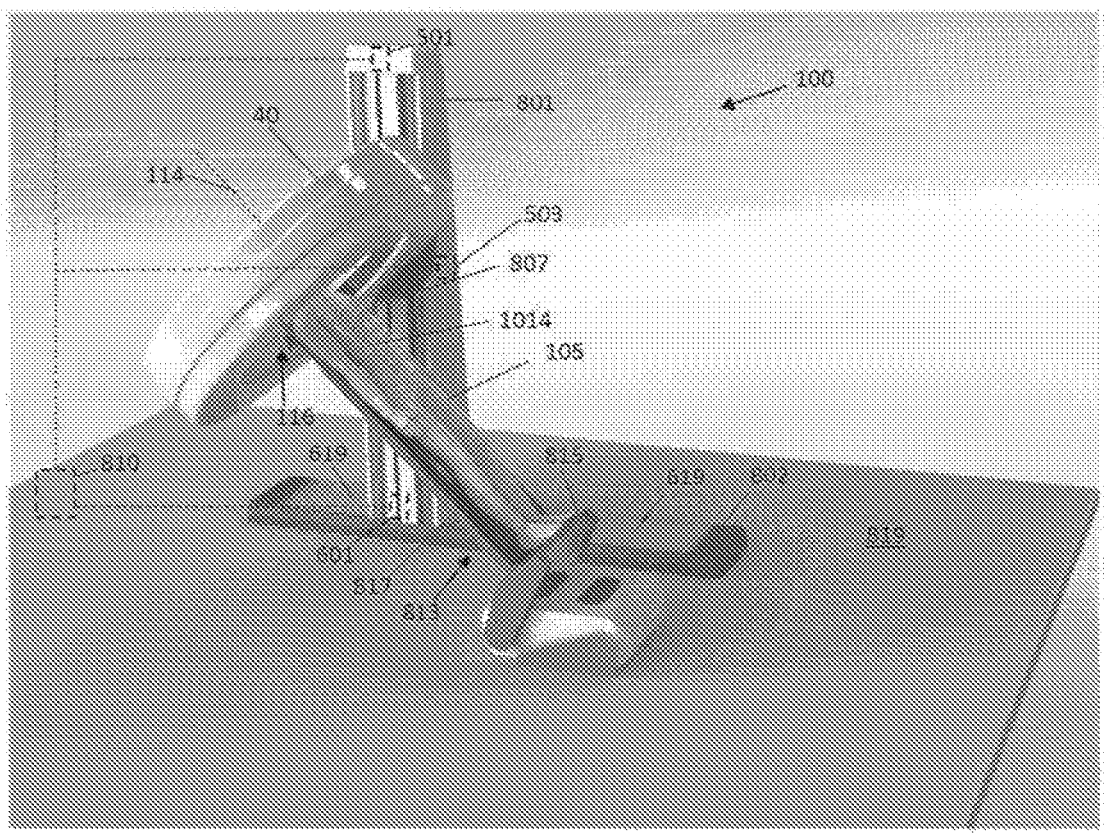
FIGS. 4A-4C illustrate the multi-axis x-ray CT imaging device performing a scan of a patient in an oblique direction.
Figure 4B:
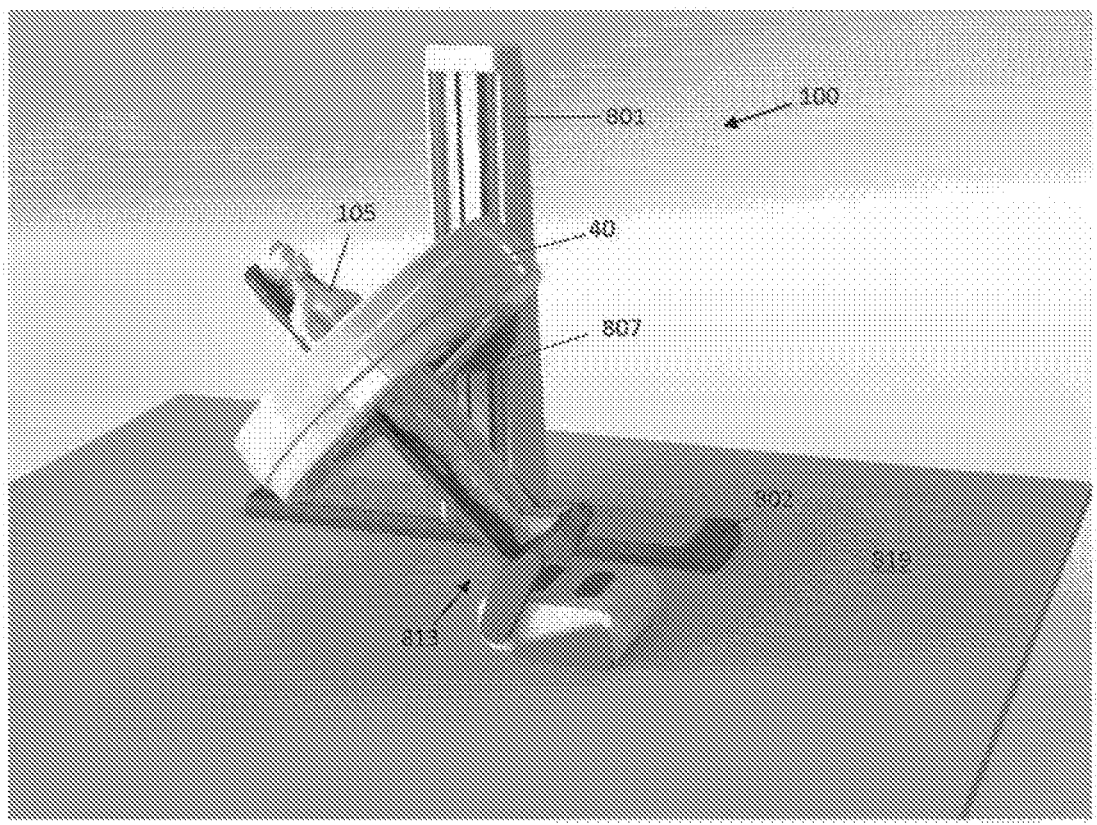
Figure 4C:
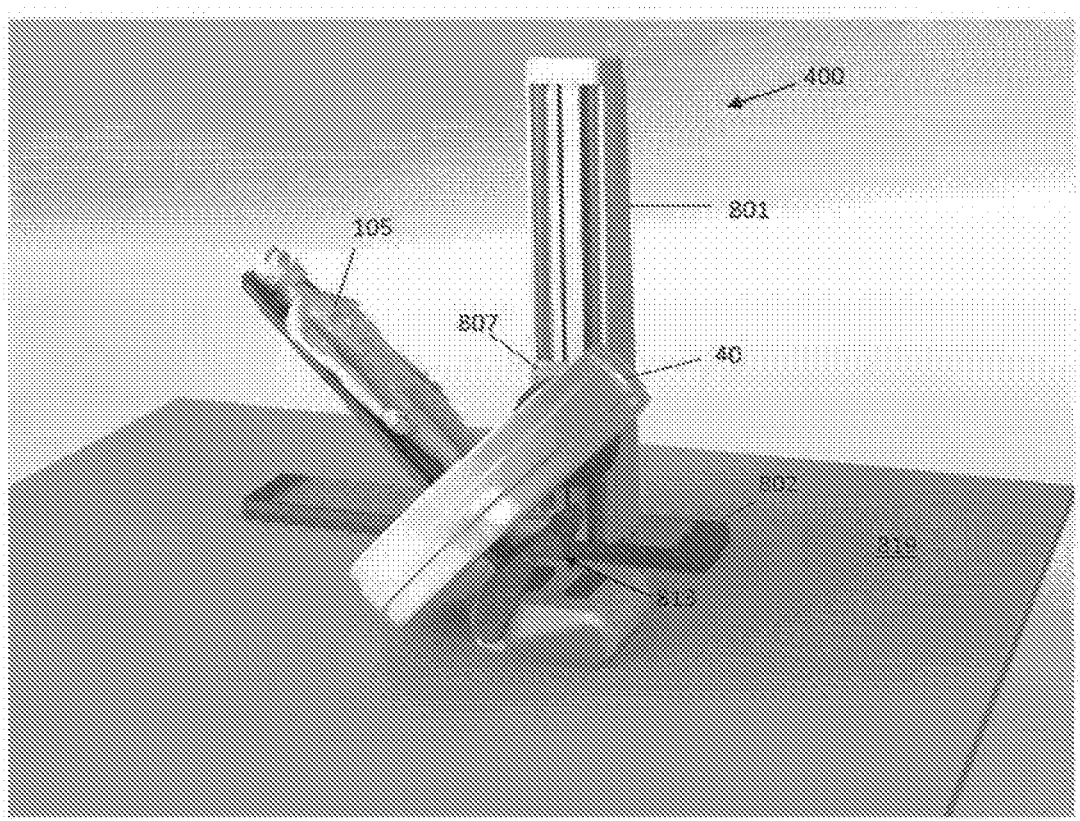

FIGS. 4A-4C illustrate the system 100 performing an imaging scan of a patient 105 along a tilted axis. The patient 105 may be supported by the patient support 813 at an oblique angle such that an axis 1014 extending lengthwise through the patient 105 is neither parallel or perpendicular to the floor 819. This may be achieved, for example, by rotating (tilting) the patient support 813 and patient 105 from a standing position (as shown in FIGS. 2A-2C) or rotating (tilting) the patient support 813 and patient 105 upwards from a lying position (as shown in FIGS. 3A-3C). The controller 810 may control the second drive mechanism 502 to rotate (tilt) the gantry 40 with respect to the support column 801 such that the imaging axis 114 through the bore 116 is parallel to, and optionally collinear with, the patient axis 1014. The system 100 may perform an imaging scan (e.g., a helical x-ray CT scan) of the patient 105 by moving the gantry 40 in the direction of the tilted patient axis 1014 while maintaining a fixed angle between the gantry 40 and axis 1014. In various embodiments, the controller 810 of the imaging system 100 may provide a coordinated movement of the gantry 40 relative to the support column 801 in a vertical direction with a movement of the gantry 40 and support column 801 relative to the base 802 in a horizontal direction. The controller 810 may include logic configured to determine the relative vertical and horizontal displacement of the gantry 40 needed to move the gantry 40 along the tilted axis 1014. The controller 810 may send control signals to the first drive mechanism 501 and to the third drive mechanism 601 to provide coordinated vertical and horizontal displacement of the gantry 40. Where the angle of the tilted axis 1014 is known or may be determined, the controller 810 may use simple trigonometric relations to determine the vertical and horizontal displacement of the gantry 40. As in the embodiment of FIGS. 4A-4C, for example, where the tilted axis 1014 is at an angle of 60° relative to horizontal, each cm of the scan along the axis 1014 may include a vertical displacement of the gantry 40 relative to the support column 801 of ~0.87 cm (i.e., sin 60°) and a horizontal displacement of the gantry 40 and support column 801 relative to the base 802 of 0.5 cm (i.e., cos 50°). Thus, the imaging system 100 may perform a scan at any tilt axis 1014, and in embodiments may perform scans along complex axes, such as along a multi-angled or curved axis.

FIGS. 4A-4C illustrate the system 100 performing an imaging scan of a patient 105 along a tilted axis 1014. In particular, for an x-ray CT imaging system, the x-ray source and detector may rotate within the gantry 40 around the patient 105 while the gantry 40 is displaced in both vertical and horizontal directions to perform a helical scan of the patient 105 along a tilted axis 1014. The patient may be supported on a patient support 813 that may be tilted such that the second portion 817 of the patient support 813 may extend parallel to the tilted axis 1014. The gantry 40 may be tilted on the support column 801 to align the gantry imaging axis 814 with the tilted axis 1014. The gantry 40 may be moved in both a vertical and horizontal direction from a first position as shown in FIG. 4A with the gantry 40 located over the head of the patient 105, to a second position as shown in FIG. 4B with the gantry 40 located over the mid-section of the patient 105, to a third position as shown in FIG. 4C with the gantry 40 located over the feet of the patient 105. The system 100 may perform scan over the full length of the patient 105 or any selected portion thereof.

Figure 5A:
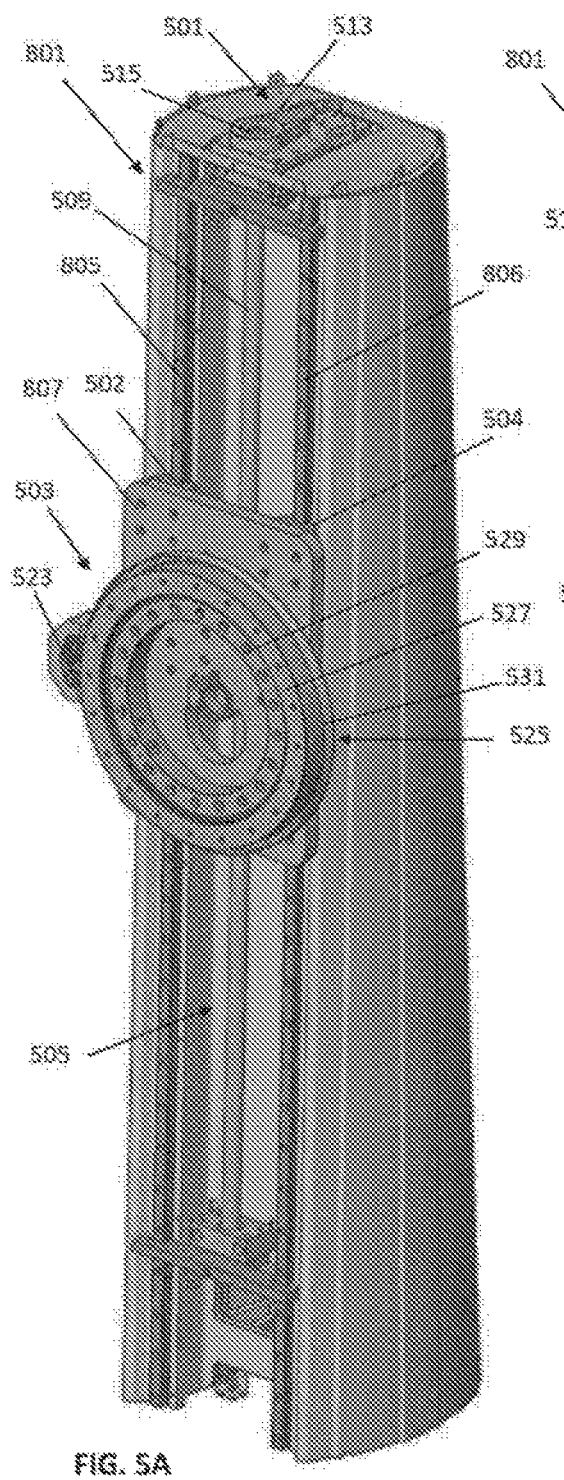
FIGS. 5A-5D illustrate a vertical support column for an x-ray gantry according to an embodiment.
Figure 5B:
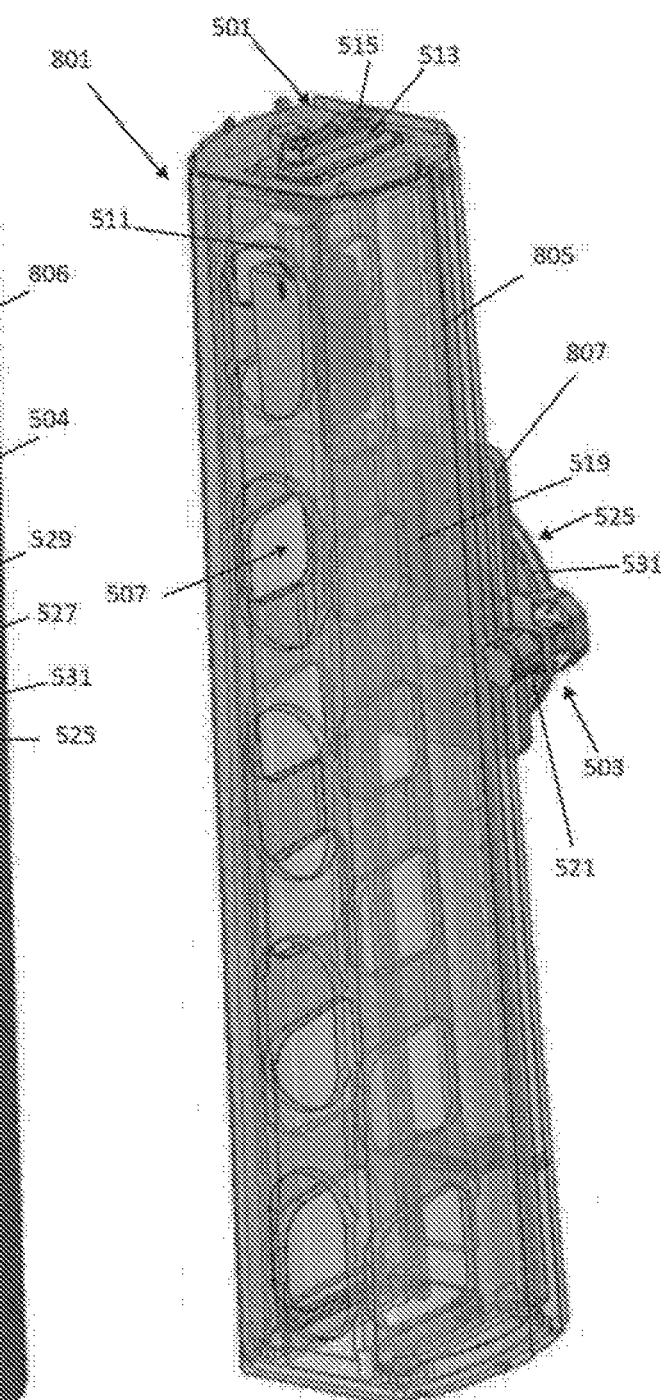
Figures 5C, 5D:
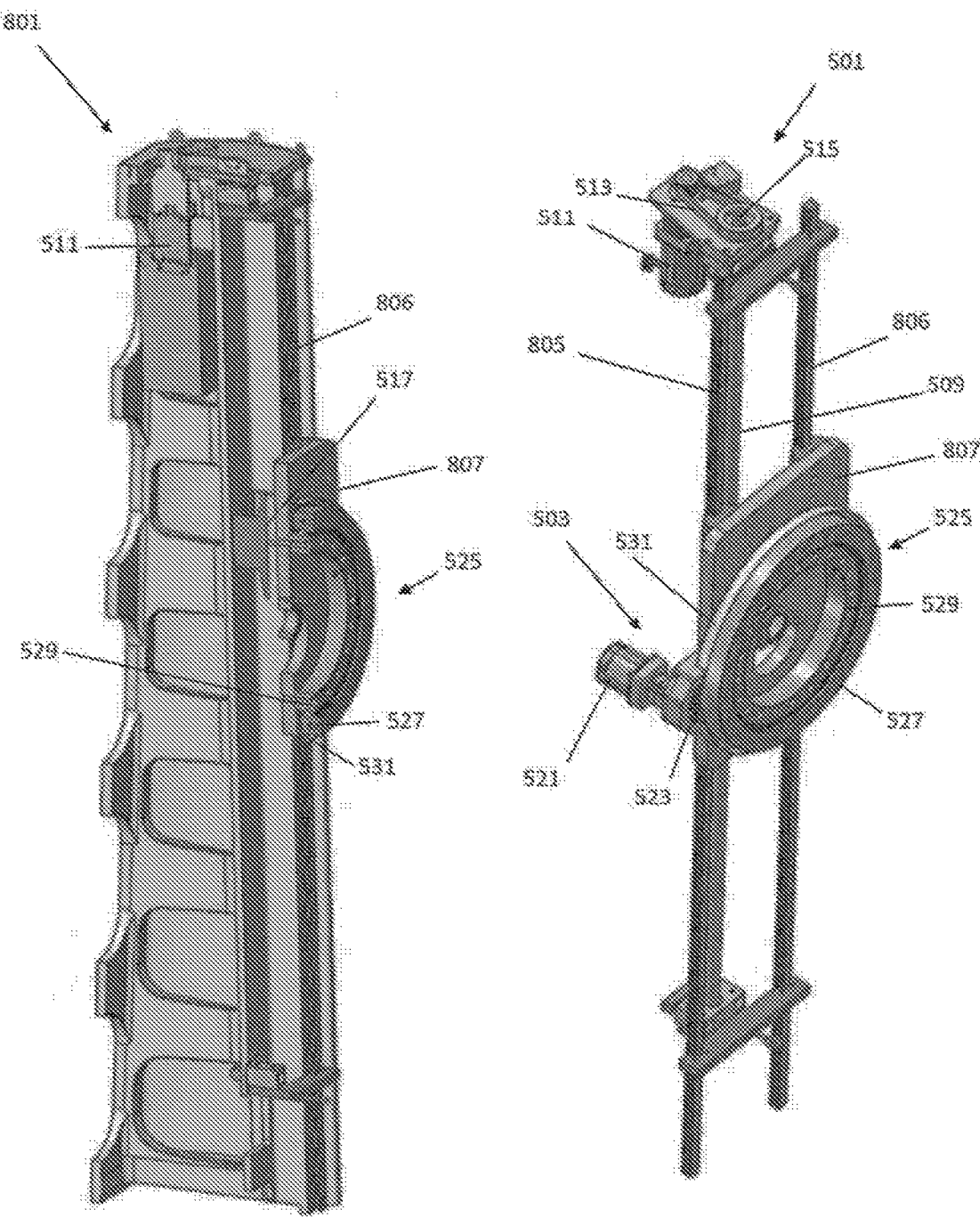

FIGS. 5A-5D illustrate an example of a support column 801 for a multi-axis imaging system. FIG. 5A is a front perspective view of a support column 801. FIG. 5B is a rear, partially-transparent perspective view of the support column 801 showing an interior portion thereof. FIG. 5C is a cross-section view taken lengthwise through the support column 801. FIG. 5D illustrates the first and second drive mechanisms 501, 503 with the surrounding support structure of the support column 801 removed.

The support column 801 may be formed of a high-strength structural material, such as aluminum. The support column 801 may include a hollow interior that may form one or more interior housings or compartments. In the embodiment of FIGS. 5A-5C, the support column 801 may include a first interior housing 505 that extends lengthwise in a front portion of the support column 801, and at least one second interior housing 507 in a rear portion of the support column. As shown in FIG. 2A, for example, a front cover 809 may cover the first interior housing 505, and an elongated opening or slot 811 may provide access to the first interior housing 505. The parallel rails 805, 806 which are engaged by the bearing elements 502, 504 of the carriage 807 may be attached to the front face of the support column 801. In some embodiments, the beds on which the rails 805, 806 are mounted may be counter-machined to offset any deflection of the support column 801 that may result from the load of the cantilevered gantry 40 as it travels up and down the column 801.

The first drive mechanism 501 for driving the vertical translation of the gantry 40 may be located on the support column 801. The first drive mechanism 501 may comprise a linear actuator, such as a lead screw or ball screw system. As shown in FIGS. 5A and 5D, a threaded shaft 509 may extend lengthwise within the first interior housing 505 of the support column 801. A motor 511, which may be located in the second interior housing 507 of the support column 801, may be geared into the threaded shaft 509 to drive the rotation of the shaft 509. In one embodiment, the motor 511 may drive a toothed belt 513 that may engage with a sprocket wheel 515 to drive the rotation of the threaded shaft 509. An arm 517 may extend from the carriage 807 into the first interior housing 505 (e.g., through the opening 811 shown in FIG. 2A). A nut 519 on the end of the arm 517 may engage with the threaded shaft 509. The rotation of the threaded shaft 509 may cause the nut 519 to reciprocate up and down along the length of the shaft 509. The reciprocation of the nut 509 on the shaft 519 may drive the vertical displacement of the carriage 807 and gantry 40 with respect to the support column 801. A controller 810 (see FIG. 4A) may control the operation of the first drive mechanism 501 and thereby control the vertical displacement of the gantry 40. The controller may receive position feedback signals indicative of the position of the gantry 40 along the support column 801, such as from a linear encoder.

The first drive mechanism 501 may be non-backdrivable under normal and/or rated operating loads (which could be, for example, up to about 6500 lbs.). This may provide improved safety of the system 100. In embodiments, the first drive mechanism 501 may include a non-backdrivable lead screw. Alternately, the first drive mechanism 501 may be a backdrivable actuator, such as a ball screw. An additional safety mechanism, such as a spring-set brake, may be utilized to prevent backdriving under load.

The second drive mechanism 503 for driving the rotation 40 of the gantry 40 relative to the support column 801 may be located on the carriage 807. In the embodiment of FIGS. 5A-5D, a motor 521 may be attached to one side of the carriage 807. The motor 521 may be geared into a sprocket wheel 523 that is adjacent to the outer race 527 of a rotary bearing 525. The outer race 527 of the bearing 525 may be attached to the gantry 40 and the inner race 529 of the bearing 525 may be attached to the carriage 807. A toothed belt 531 may extend over at least a portion of the outer circumference of the outer race 527 and may engage with a toothed surface of the outer race 527. The belt 531 may be looped over the sprocket wheel 523 that is driven by the motor 521 such that the rotation of the sprocket wheel 523 in a clockwise or counterclockwise direction causes a corresponding rotation of the outer race 527 and gantry 40 relative to the inner race 529, carriage 807 and support column 801. The second drive mechanism 503 preferably includes minimal lash between the belt 531, sprocket wheel 523 and toothed surface of the outer race 527 to enable precise rotational control of the gantry 40. In embodiments, the belt 531 may not be continuous, and opposing ends of the belt 531 may be bolted or clamped to the outer race 537 to minimize slippage and/or backlash. In embodiments, the belt 531 may be clamped to enable at least about 270°, including about 300° or more, of rotation of the gantry 40 relative to the support column 801. In some embodiments, a brake system may be selectively engaged to hold the rotational (tilt) position of the gantry 40 (e.g., during a scan). The controller 810 (see FIG. 10A) may control the operation of the second drive mechanism 503 and thereby control the rotational displacement of the gantry 40. The controller may receive position feedback signals indicative of the rotational position of the gantry 40 with respect the support column 801, such as from a rotary encoder.

FIGS. 6A-6B illustrate a base 802 of a multi-axis imaging system 100 according to an embodiment. The base 802 may include a generally rectangular support frame 602. A pair of parallel support rails 603, 605 may extend lengthwise along the base 802. The support rails 603, 605 may support the support column 801 and inhibit deflection as the support column 801 traverses along the length of the base 802. A pair of guide rails 607, 609 may extend along a bottom surface of the base 802 and may be parallel to the support rails 603, 605. A platform 611 may be located over the support rails 603, 605. The support column 801 may be attached (e.g., screwed or bolted) to the upper surface of the platform 611. The platform 611 may include bearing elements 613 (e.g., bearing slides) that engage with the guide rails 607, 609 to provide linear motion of the platform 611, support column 801 and gantry 40 along the length of the base 802.

The third drive mechanism 601 for driving the horizontal translation of the gantry 40 and support column 801 may be located on the base 802. The third drive mechanism 601 may comprise a motor 613 that may be attached to the platform 611. The motor 613 may be geared into a sprocket wheel 615. A drive belt 617 may extend lengthwise along the bottom surface of the base 802. A portion of the drive belt 617 adjacent to the platform 611 may be looped over and engage with the sprocket wheel 615 that is driven by the motor 613. The driving of the sprocket wheel 615 by the motor 613 may cause the sprocket wheel 613 and platform 611 to traverse up and down the length of the drive belt 617, thereby driving the translation of the platform 611, support column 801 and gantry 40 along the length of the base 802. The controller 810 (see FIG. 4A) may control the operation of the third drive mechanism 601 and thereby control the translation of the gantry 40 and support column 801 relative to the base. The controller 810 may receive position feedback signals indicative of the translational position of the gantry 40 and support column 801 on the base 802, such as from a linear encoder.

The base 802 may include a cover 619 to protect the internal components of the base 802. The cover 619 may be made of a flexible material and may be wound on a spool 621 as shown in FIG. 6A. The spool 621 may be enclosed within a housing 623 located at an end of the base 802. One end of the cover 619 may be attached to the platform 611 and/or the support column 801 (e.g., using hooks or similar attachment mechanism). The spool 621 may be spring-loaded to maintain a suitable tension on the cover 619. As the support column 801 translates away from the housing 623, the cover 619 may be extended from the housing 623 by being unwound from the spool 621 and as the support column translates towards the housing 623 the cover 619 may be retracted into the housing 623 by being wound onto the spool 621 (e.g., similar to the operation of a roller shade for windows). The base 802 may include a pair of covers 619 attached to opposite sides of the support column 801, where the covers 619 extend and retract from opposite sides of the base 802 as the support column 801 translates. FIGS. 1-4C illustrate the base with extending/retracting covers 619 attached to the support column 801.

Figure 7A:
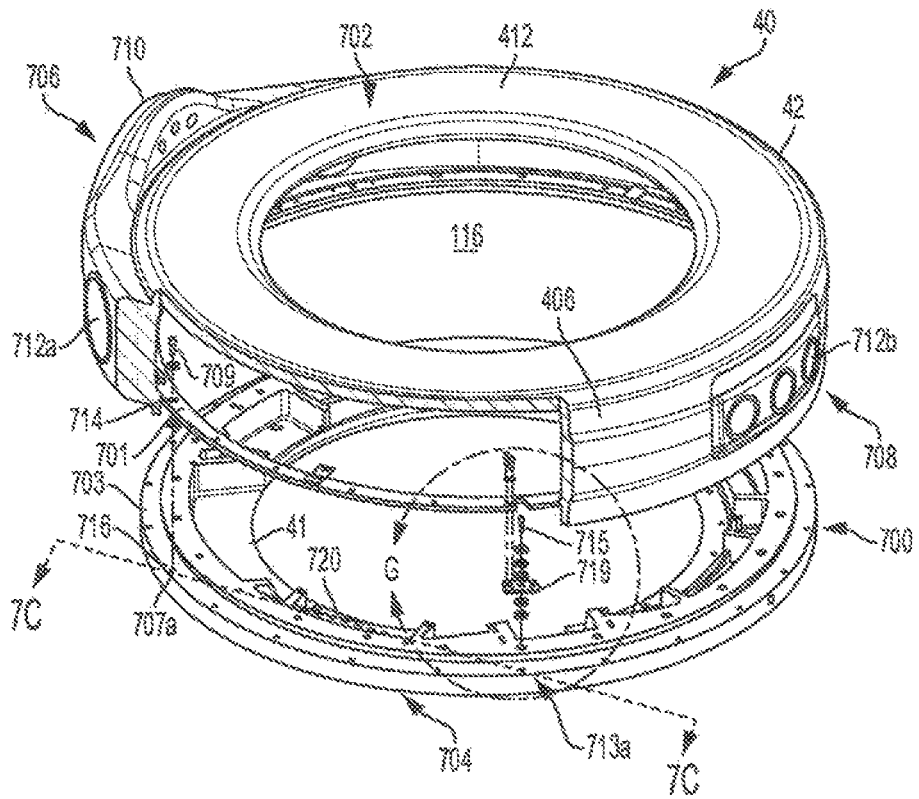
FIG. 7A-7E illustrate a gantry and a bearing assembly for a multi-axis imaging system according to an embodiment.

FIGS. 7A-7E illustrate a gantry 40 of a multi-axis imaging system 100 according to an embodiment. FIG. 7A is an exploded view of a gantry 40 that illustrates an outer shell 42 of the gantry, a rotor 41 and a bearing assembly 700. The outer shell 42 may comprise a high-strength structural material, such as aluminum. The outer shell 42 may have an outer circumferential wall 406 that may extend around the periphery of the gantry 40 to enclose the rotating components of the gantry 40 (e.g., x-ray source, detector, etc.), which may be attached to the rotor 41. The outer shell 42 may also include a side wall 412 that may extend from the outer circumferential wall 406 to a bore 116 of the gantry 40 and may enclose the rotating components around one side of the rotating portion. The side wall 412 may form a first outer face 702 of the gantry 40 and may at least partially define the size of the bore 116 of the gantry. A lip portion 701 may extend from the outer circumferential wall 406 around the interior periphery of the gantry shell 42. The lip portion 701 may provide a mounting surface of the bearing assembly 700, as described further below. The lip portion 701 may be offset from the second outer face 704 of the gantry 40 by a distance sufficient to accommodate at least a portion of the bearing assembly 700 inside the outer circumferential wall 406 of the gantry shell 42.

The outer shell 42 of the gantry 40 is shown in a partial cutaway view through the outer circumferential wall 406 in FIG. 7A. As shown in FIG. 7A, the outer circumferential wall 406 may have a larger cross-section thickness at a proximal end 706 of the gantry 40 where the gantry 40 is attached to the support column 801 than at the distal or unsupported end 708 of the gantry 40. The proximal end 706 of the gantry 40 may include a generally circular-shaped flange portion 710 that may be attached to the outer race 527 of the rotary bearing 525 shown in FIGS. 5A-5D.

One or more openings 712 may be provided through the outer circumferential wall 406 as shown in FIG. 7A. The openings 712 may provide air-flow cooling of the components within the gantry 40. In one embodiment, a first set of one or more openings 712a may be located at the proximal end 706 of the gantry 40 and a second set of one or more openings 712b may be located at the distal end 708 of the gantry 40. One or more fans (not illustrated) may be located adjacent to the second set of opening(s) 712b and may operate to suck ambient air in through the first set of opening(s) 712a, over the components within the gantry 40 and out through opening(s) 712b. Alternately or in addition, one or more fans may be located adjacent to the first set of opening(s) 712a and may blow air through the gantry 40 and out through opening(s) 712b. In further embodiments, the direction of airflow may be reversed, such that air is sucked into the gantry 40 through opening(s) 712b and exits the gantry 40 through openings 712(a).

Figure 7B:
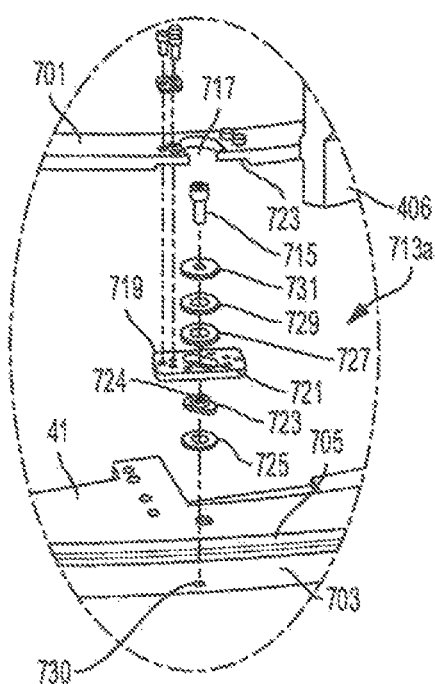
Figure 7C:
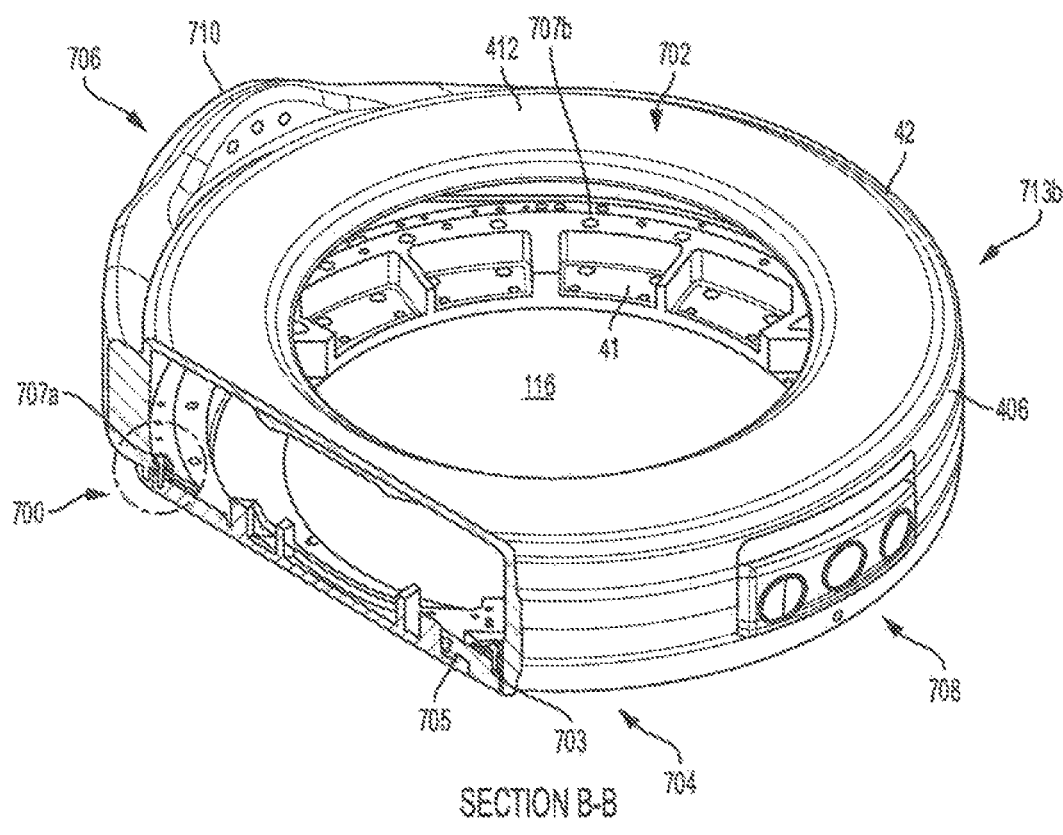

The bearing assembly 700 according to one embodiment is shown in FIGS. 7A and 7C. FIG. 7A is an exploded view showing the bearing assembly 700 attached to the rotor 41. FIG. 7C illustrates the assembled gantry 40 in a partial cut-away view showing the bearing assembly 700 attached to the rotor 41 and to the gantry shell 42. As shown in FIG. 7C, the bearing assembly 700 includes a first race 703 that is attached to the lip portion 701 of the outer shell 42 of the gantry 40, and a second race 705 that is attached to the rotor 41. A bearing element is provided between the first race 703 and the second race 705, and is configured to allow the second race 705 (along with the rotor 41 to which it is attached) to rotate concentrically within the first race 703, preferably with minimal friction, thereby enabling the rotor 41 to rotate with respect to the outer shell 42 of the gantry 40. In the embodiment of FIGS. 7A and 7C, the second race 705 may be a separate component that is firmly secured around the outer circumference of the rotor 41 (e.g., using mechanical fasteners). Alternately, the second race 705 may be formed as an integral part of the rotor 41.

In various embodiments, the first race 703 of the bearing assembly 700 may be mounted to the outer shell 42 of the gantry 40 using a limited suspension system. The suspension system may be configured to accommodate a limited amount of bending/deflection of the cantilevered gantry 40 between the proximal 706 and distal 708 ends of the gantry 40 while ensuring that the bearing assembly 703 rotates within a plane. The present inventors have discovered that attaching an imaging gantry 40 to a support structure 801 at only one end of the gantry 40 in a cantilevered manner may result in a small amount of deflection or bending of the gantry 40 due to the gravity-induced bending moment of the gantry 40. When the gantry 40 is rotated out-of-line with the vertical support column 801, such as for performing a vertical scan as shown in FIGS. 2A-2C or a scan along a tilted axis as shown in FIGS. 3A-3C, the direction of gantry 40 deflection may include a component that is normal to the scan plane of the imaging components (e.g., x-ray source and detector) rotating within the gantry 40. This downward curve or bend of the gantry and bearing on which the rotating components rotate may introduce a sufficiently large "wobble" effect to these components as they rotate between the proximal 706 and distal 708 ends of the gantry 40 to negatively affect image quality of the scan.

Various embodiments include a limited suspension system between the gantry shell 42 and the bearing assembly 700 to provide a small amount of compliance between these components in the direction of gantry deflection such that the bearing assembly 700 may continue to rotate in a plane when the gantry shell 42 is subject to gravity-induced deflection. In the embodiment of FIGS. 7A-7E, this may be achieved by attaching the bearing assembly 700 to the gantry shell 42 at a limited number of attachment points and allowing the portion of the bearing assembly 700 proximate to the distal end 708 of the gantry 40 to effectively "float" over a limited range with respect to the gantry shell 42. In the embodiment of FIGS. 7A-7E, the lip portion 701 of the gantry shell 42 is attached to the first race 703 of the bearing assembly 700 in four locations around the periphery of the gantry 40. It will be understood that the disclosed embodiment is merely exemplary and various embodiments may include more than or less than four attachments points between the gantry shell 42 and the bearing assembly 700.

Figure 7D:
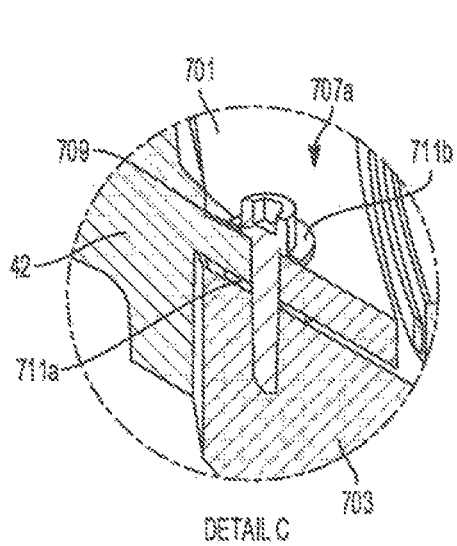

In the embodiment of FIGS. 7A-7E, the lip portion 701 of the gantry shell 42 may be fastened to the first race 703 of the bearing assembly 700 in two locations 707*a*, 707*b* that are more proximate to the proximal end 706 of the gantry 40 than to the distal end 708 of the gantry 40. The two locations 707*a*, 707*b* are visible in FIG. 7C. The two locations 707*a*, 707*b* may be located on opposite sides of the gantry 40 and may be equidistant from the proximal end 706 of the gantry 40. The lip portion 701 may be rigidly fastened to the first race 703 at locations 707*a*, 707*b* using mechanical fasteners, such as a screw 709 that may pass through an opening 714 in the lip portion 701 and into an opening 716 (e.g., a threaded opening) in first race 703. A pair of washers 711*a*, 711*b* may be located between the bottom surface of the lip portion 701 and the top surface of the first race 703 and between the top surface of the lip portion 701 and the head of the screw/bolt 709, respectively. The screw 709 may be tightened against the top surface of the lip portion 701 (via washer 711*b*) to rigidly and securely attach the lip portion 701 to the first race 703 at locations 707*a*, 707*b*, as shown in the cross-section view of FIG. 7D. Washer 711*a* may provide a small gap between the bottom surface of the lip portion 701 and the top surface of the first race 703, as shown in FIG. 7D.

The bearing assembly 700 may be suspended from the gantry shell 42 at two additional locations 713*a*, 713*b* that are more proximate to the distal end 708 of the gantry 40 than to the proximal end 706 of the gantry 40. FIGS. 7A-7C and 7E illustrate the attachment of the lip portion 701 of the gantry shell 42 to the first race 703 of the bearing assembly 700 at location 713*a*. The lip portion 701 may be attached to the first race 703 at location 713*b* in the same or similar fashion as shown in FIGS. 7A-7C and 7E. Location 713*b* may be located on the opposite side of the gantry 40 from location 713*a*. Locations 713*a* and 713*b* may be equidistant from the distal end 708 of the gantry 40. In embodiments, attachment locations 707*a* and 713*a* may extend along a secant line 720 of the circular gantry 40. The secant line 720 may be parallel to a midline of the gantry 40 extending from the proximal end 706 to the distal end 708 of the gantry 40. Attachment locations 707*b* and 713*a* may extend along a second secant line of the gantry 40, where the second secant line may also be parallel to the midline extending between the proximal 706 and distal ends 708 of the gantry 40. The first and second secant lines may be equidistant from the midline.

Figure 7E:
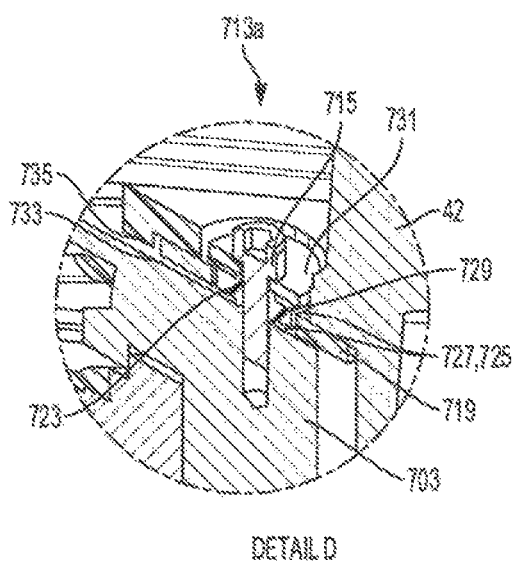

FIG. 7B is an exploded view of the components used to attach the lip portion 701 to the first race 703 at location 713*a*. FIG. 7E is a cross-section view showing the lip portion 701 attached to the first race 703 at location 713*a*. As shown in FIGS. 7B and 7E, the lip portion 701 and first race 703 may be attached using a mechanical fastener, such as a screw 715, that may be similar or identical to the screw 709 used to fasten the lip portion 701 to the first race 703 at locations 707*a*, 707*b*. The screw 709 may pass through a relatively large diameter opening 717 in the lip portion 701 of the gantry shell 42. A metal (e.g., steel) plate 719 having a slot 721 may be attached to the bottom surface of the lip portion 701 using mechanical fasteners (e.g., screws or bolts). The bottom surface of the lip portion 701 may include a recess 723 surrounding the opening 717 to accommodate the plate 719. The slot 721 may be oriented along the direction of gravity-induced deflection of the cantilevered gantry 40. For example, the slot 721 may extend along the secant line 720 of the gantry 40 that intersects attachment locations 707*a* and 713*a*.

A bushing 723, which may be a bronze bushing, may be located within the slot 721 of the plate 719. The bushing 723 may be dimensioned slightly smaller than the slot 721 along the length of the slot 721 so that there is some degree of compliance between the bushing 723 and the plate 719 in the direction of gantry deflection. This is illustrated in the cross-section view of FIG. 7E. There may be less compliance between the bushing 723 and the plate 709 along the width of the slot 721. Thus, the bushing 723 may be held tight between the side walls of the slot 721 when the gantry 40 is rotated up into the configuration of FIGS. 3A-3C (e.g., for performing a horizontal scan). A first washer 725, which may be a bronze washer, may be located between the bottom surface of the plate 719 and the top surface of the first race 703, and may surround a central opening 724 through the bushing 723. A second washer 727, which may also be a bronze washer, may be located on the top surface of the plate 719 and may surround the central opening 724 through the bushing 723. A Belleville spring washer 729 may be located above the second washer 727 and may surround the central opening 724 through the bushing 723. A third washer 731, which may be a steel washer, may be located above the Belleville spring washer 729.

The screw 715 may be inserted through the third (e.g., steel) washer 731, the Belleville spring washer 729, the second (e.g., bronze) washer 727, the central opening 724 of the bushing 723 and the first (e.g., bronze) washer 725 and into an opening 730 (e.g., a threaded opening) in first race 703. The screw 715 may be fastened against the top surface of the plate 719 (via washers 731, 729 and 727) to attach the plate 719 to the first race 703 at location 713a, as shown in FIG. 7E. The plate 719 may be sandwiched between the first and second washers 725 and 727. The spring washer 729 may be pre-loaded to maintain the entire stack in compression. The plate 719 may be separated from the top surface of the first race 703 by a gap 733 defined by the first washer 725. A second gap 735 may separate the bottom surface of the lip portion 701 from the top surface of the first race 703 as shown in FIG. 7E.

The attachment configuration shown in FIGS. 7B and 7E may provide a secure attachment between the gantry shell 42 and the first race 703 of the bearing assembly 700 while allowing the gantry shell 42 to bend or deflect over the bearing assembly without transferring any bend or curvature in the gantry shell 42 to the bearing assembly 700. This may be achieved by suspending the bearing assembly 700 from the gantry shell 42 in a limited number of attachment locations that are sufficiently spaced to adequately support the bearing assembly 700 and the rotor 41 as it rotates within the gantry 40. This contrasts with prior attachment techniques in which the bearing assembly 700 is rigidly secured to the gantry shell 42 at regular intervals (e.g. every 15-30° or so) around the periphery of the gantry 40. In addition, the gap 735 provided between the lip portion 701 and the first race 703 at the distal-most attachment points 713a, 713b may be sufficient to prevent the lip portion 701 from imparting a bending force on the first race 703 at the distal end 708 of the gantry 40. Thus, bearing assembly 700 may remain flat over the entire gantry 40 even when the gantry shell 42 bends due to gravity.

Figure 8:
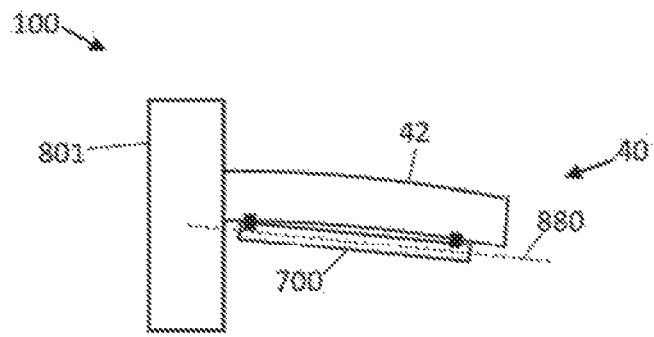
FIG. 8 schematically illustrates a bearing assembly attached to a gantry shell according to an embodiment.

This is schematically illustrated in FIG. 8, which is a side view of a cantilevered gantry 40 mounted to a support column 801. It will be understood that FIG. 8 is not necessarily to scale and is intended to provide an exaggerated view of the amount of bending of the gantry 40. For example, for an x-ray CT system, the amount of gantry deflection between the fixed (proximal) and free (distal) ends of the gantry may be 1-2 mm or less. As shown in FIG. 8, by suspending the bearing assembly 700 for the rotor from the gantry shell 42 at a plurality of spaced-apart locations as described above, the bearing assembly 700 is not influenced by the curvature of the gantry shell 42. Thus, the bearing assembly 700 and the rotor may rotate in a plane 880, as illustrated by the dashed line. The plane 880 of rotation of the bearing assembly 700 and rotor may be tilted from a horizontal plane, as shown in FIG. 8. This tilt may be corrected for in the software used to process the image data obtained by the imaging system.

Alternately or in addition, the tilt angle of the plane of rotor rotation may be compensated for by mounting the gantry 40 at an angle with respect to the support column 801. For example, the carriage 807 to which the gantry 40 is attached may have an angled front surface that compensates for the tilt angle of the rotor so that the scan plane is horizontal.

Figure 9:
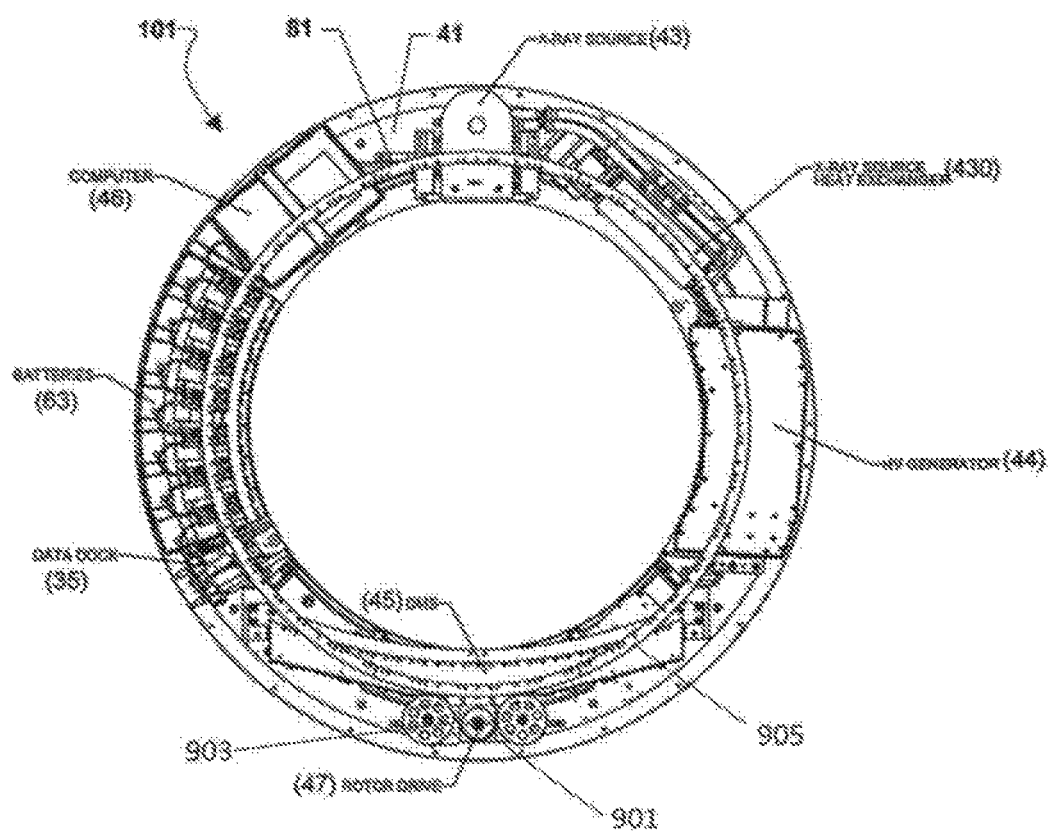
FIG. 9 illustrates components mounted to a rotor according to an embodiment.

FIG. 9 illustrates a rotor 41 for an x-ray CT imaging system having a plurality of components mounted thereto. The system may be a multi-axis system 100 as described above. The rotor 41 may rotate within a gantry 40, and may be mounted within the gantry 40 on a bearing assembly 700 as described above with reference to FIGS. 7A-7E. In particular, the rotor 41 may be mounted to the second race 705 of the bearing assembly 700 shown in FIG. 7C using suitable fasteners, such as bolts or screws.

The rotor 41 shown in FIG. 9 includes an x-ray source 43, a high-voltage generator 44, a heat exchanger 430, an x-ray detector 45, a power supply 63 (e.g., battery system), a computer 46, a rotor drive mechanism 47, and a docking system 35 (e.g., for providing intermittent power/data connection between rotating and non-rotation portions of the system). It will be understood that the components described and illustrated are merely exemplary, and other embodiments may omit one or more of these components and may utilize other additional components. For example, in embodiments, power for the rotating portion 101 may be provided by a slip ring or cable system, so that a power supply 63 on the rotating portion 101 may not be needed. In some embodiments, power and/or data may be continuously transferred between the rotating and non-rotating portions via cable, slip ring or wirelessly, in which case the power supply 63, computer 46 and/or docking system 35 may not be included. Further, the rotation of the rotor may be provided by a drive system on the non-rotating portion, in which case the rotor drive mechanism 47 on the rotor 41 may not be included. Also, it will be understood that other types of imaging systems, such as MRI systems, may use other suitable components for imaging, as are known in the art.

In embodiments, the x-ray source 43 and detector 45 may be configured to perform a helical x-ray CT scan. The detector 45 may comprise a plurality of x-ray sensitive detector elements arranged in a semicircular arc, with the arc center coinciding with the focal spot of the x-ray source. In some embodiments, the x-ray detector may be a flat panel detector, and the system may be configured to perform real time x-ray fluoroscopic and/or cone beam imaging of an object within the bore of the gantry.

In the embodiment of FIG. 9, during an imaging scan, the rotor 41 rotates within the interior of the gantry, while the imaging components such as the x-ray source 43 and x-ray detector 45 obtain imaging data for an object positioned within the bore 116 of the gantry, as is known, for example, in conventional X-ray CT scanners. The rotor drive mechanism 47 may drive the rotation of the rotor 41 around the interior of the gantry 40. In embodiments, the rotor drive mechanism 47 may include a drive wheel 901 that engages with a belt 903. The belt 903 may extend around the gantry 40 on a circular rail 905 that may be fixed to the side wall 412 of the gantry shell 42 (see FIG. 7A). The rotor drive mechanism 47 may be controlled by a system controller that controls the rotation and precise angular position of the rotor 41 with respect to the gantry 40, preferably using position feedback data, such as from an encoder device.

Figure 10A:
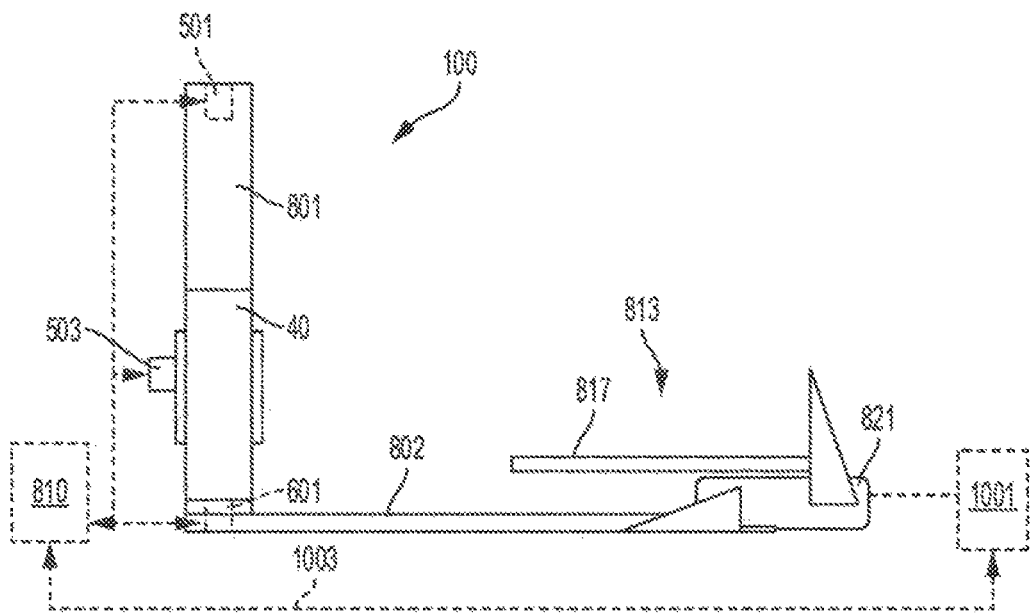
FIGS. 10A-10K illustrate methods of operating a multi-axis imaging system and moveable patient support to perform an imaging scan of a patient.

FIGS. 10A-10K illustrate methods of operating an imaging system 100 to perform an imaging scan of a patient 105 according to various embodiments. The patient 105 may be located on a patient support 813 (e.g., a patient table) as described above. A control system 1001 (e.g., a processor and memory) may be operatively coupled to the patient support 813, as schematically illustrated in FIG. 10A. The control system 1001 may be located partially or completely within the patient support 813 (e.g., within the linkage member 821) and/or within one or more separate components, such as a workstation, the imaging system 100 or a mobile cart. The control system 1001 may receive positon feedback data (e.g., rotary encoder data) from the patient support 813 and may send control signals to the motor(s) of the patient support 813 to cause the motor(s) to move the patient support 813 into a desired configuration. The configuration of the patient support 813 may be a pre-set configuration (e.g., stored in the memory of the control system 1001) and/or the configuration may be controllably adjusted by a user using a suitable user input device (e.g., buttons, joystick, pendant controller, computer keyboard and/or mouse, touchscreen display, etc.).

The multi-axis imaging system 100 may also include a control system 810 (e.g., a processor and memory). The control system 810 may be coupled to and control the operation of the first drive mechanism 501, the second drive mechanism 503 and the third drive mechanism 601 to cause the relative translation and rotation of the gantry 40 with respect to the support column 801 and base 802 as described above. The control system 801 may also receive position feedback signals indicative of the relative positions and orientations of the gantry 40, support column 801 and base 802, such as from one or more encoders. The control system 810 may also control the operation of the imaging components within the gantry 40, and may for example, issue command signal(s) to perform an imaging scan.

The control system 810 may be located within the multi-axis imaging system 100, such as within the support column 801 and/or within one or more separate components, such as a workstation or a mobile cart. In some embodiments, the control system 810 for the multi-axis imaging system 100 may be co-located with the control system 1001 of the patient support 813. For example, control systems 810 and 1001 may be implemented as separate processes (e.g., software applications) which run on the same computing device.

The control system 810 for the multi-axis imaging system 100 may be coupled to the control system 1001 for the patient support 813 via a communication link 1003. The communication link 1003 may enable the control system 1001 for the patient support 813 to transmit data regarding the configuration of the patient support 813 to the control system 810 for the multi-axis imaging system 100. In embodiments, the communication link 1003 may be a bi-directional link, and the control system 810 for the multi-axis imaging system 100 may send data to the control system 1001 for the patient support 813 indicating the configuration of the multi-axis imaging system 100.

In various embodiments, the control systems 810, 1001 for the multi-axis imaging system 100 and the patient support 813 may communicate over communication link 1003 so that each of these components may always know where the other one is relative to it. This may provide an important safety feature to prevent the imaging system 100 from colliding with the patient support 813 or a patient supported thereon. In embodiments, the multi-axis imaging system 100 and the patient support 813 may be "electronically geared" such that a movement of one of these components may cause a pre-determined counter-movement of the other component. In one embodiment, the control system 1001 for the patient support 813 may be the "master" controller and the control system 810 for the imaging system 100 may be the "slave" controller. In other words, a movement of the patient support 813 may cause the control system 810 of the imaging system 100 to control the system 100 to make a corresponding counter-move.

FIGS. 10A-10K illustrate various motions of the patient support 813 and multi-axis imaging system 100. In FIG. 10A, the patient support 813 may be in a position for loading or unloading of a patient. The imaging system 100 may be in a standby or "home" position with the support column 801 and gantry 40 translated away from the patient support 813. The gantry 40 may be rotated in-line with the support column 801. The standby or "home" position of the imaging system 100 may inhibit a collision between the imaging system 100 and the patient or the patient support 813. The patient support 813 in various embodiments may be lowered to a position as shown in FIG. 10A so that the second portion 817 of the patient support 813, which can support the patient in a lying position, is at a comfortable height for loading and unloading of the patient. For example, the second portion 817 may be at a height of no more than about 50 cm, such as between 30 and 40 cm from the floor. This may allow a patient to easily climb onto or be lowered down onto the patient support 813, which may be convenient and safe for both the patient and the medical staff members.

Figure 10B:
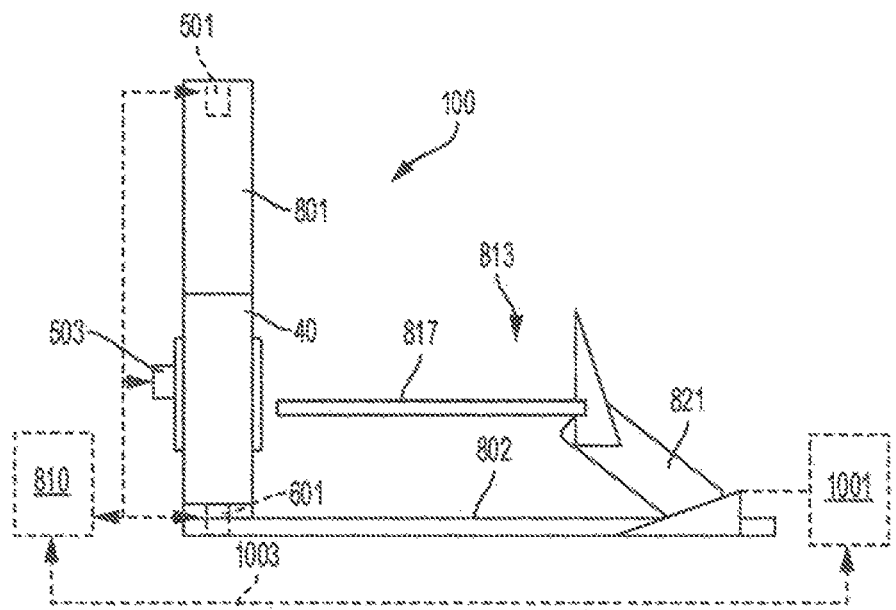
Figure 10C:
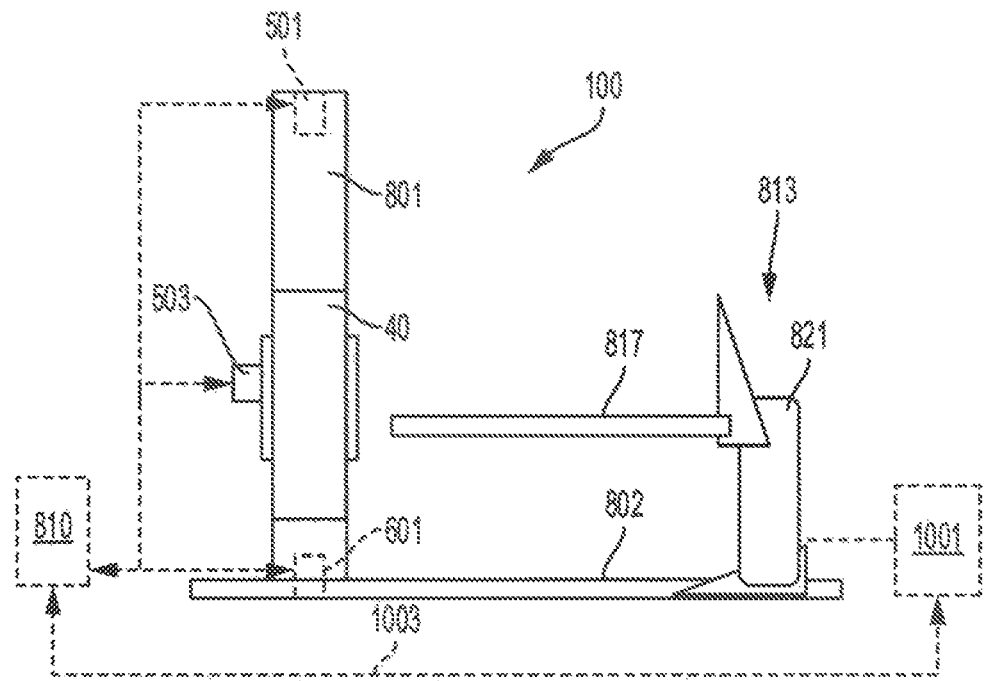

The patient support 813 may then be raised from the lowered position of FIG. 10A to a height suitable for an imaging scan (e.g., such that the patient support 813 may be positioned within the bore of the gantry 40). FIG. 10B illustrates the patient support 813 raised such that it is aligned with the bore of the gantry 40. In this configuration, the imaging system 100 is ready to perform a horizontal scan of a patient in a lying position. The patient support 813 may be raised or lowered to a suitable height for performing a scan. FIG. 10C illustrates the patient support 813 raised to a maximum height for performing a scan of a patient supported in a horizontal lying position. The control system 810 of the imaging system 100 may send control signals to the first drive mechanism 501 to cause the gantry 40 to translate vertically on the support column 801 in coordination with the movement of the patient support 813 so that the bore of the gantry 40 remains aligned with the second portion 817 of the patient support 813. In some embodiments, the control system 810 of the imaging system 100 may also send control signals to the third drive mechanism 601 to cause the support column 801 and gantry 40 to translate along the base 802 to maintain a pre-determined separation between the gantry 40 and the tip end of the second portion 817 of the patient support 813 as the patient support 813 is raised and/or lowered. In some embodiments, gantry 40 may move to maintain the outer face of the gantry 40 separated from the tip end of the of the second portion 817 of the patient support 813. Alternately, the gantry 40 may move to maintain the tip end of the second portion 817 at least partially inside the bore of the gantry 40.

Figure 10D:
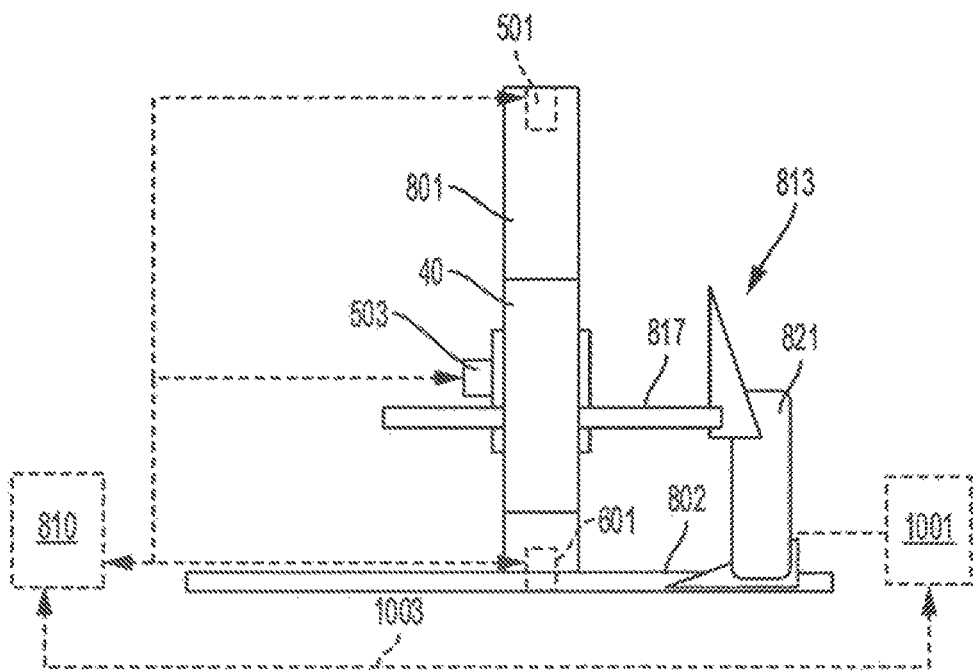

When the patient support 813 is moved to a desired configuration, the control system 1001 of the patient support 813 may send a signal to the control system 810 of the imaging system 100 indicating that the system is ready to perform a scan. The control system of the imaging system 100 may send control signals to the third drive mechanism 601 to cause the support column 801 and gantry 40 to translate along the base 802 and over the patient support 813 to perform a scan in a horizontal direction, as shown in FIG. 10D. In some embodiments, the patient support 813 may be prohibited from moving until the scan is complete.

Figure 10E:
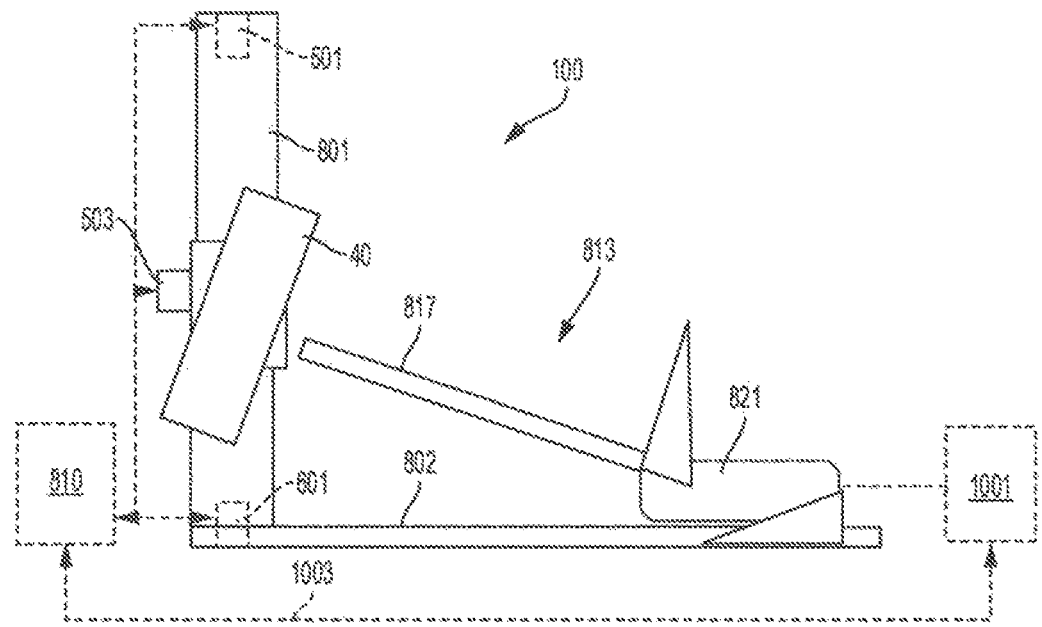
Figure 10F:
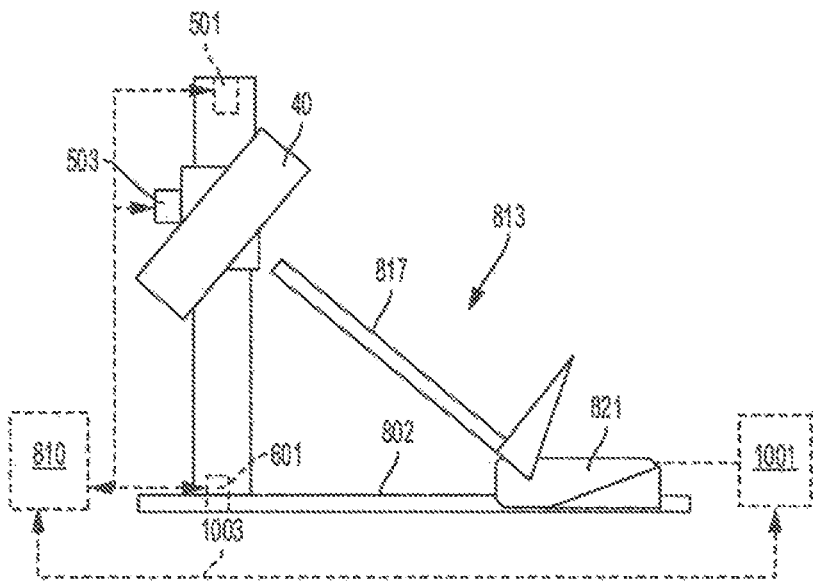

To perform a scan along a tilted axis such as shown in FIGS. 4A-4C, the patient support 813 may be pivoted upwards as shown in FIGS. 10E and 10F. In response to the movement of the patient support 813, the control system 810 of the imaging system 100 may control the first, second and third drive mechanisms 501, 503, 601 to perform a coordinated motion of the gantry 40 as shown in FIGS. 10E and 10F. In particular, the second drive mechanism 503 may rotate the gantry 40 relative to the support column 801 to maintain the bore axis of the gantry 40 aligned with the tilt angle of the patient support 813. The first and third drive mechanisms 501 and 601 may translate the gantry 40 in both a vertical and horizontal direction to maintain the bore of the gantry 40 in alignment with the tip end of the patient support 813. The gantry 40 may maintain a pre-determined separation distance from the tip end of the patient support 813 as it follows the position of the patient support 813. In some embodiments, gantry 40 may move to maintain the outer face of the gantry 40 separated from the tip end of the of the second portion 817 of the patient support 813. Alternately, the gantry 40 may move to maintain the tip end of the second portion 817 at least partially inside the bore of the gantry 40.

Figure 10G:
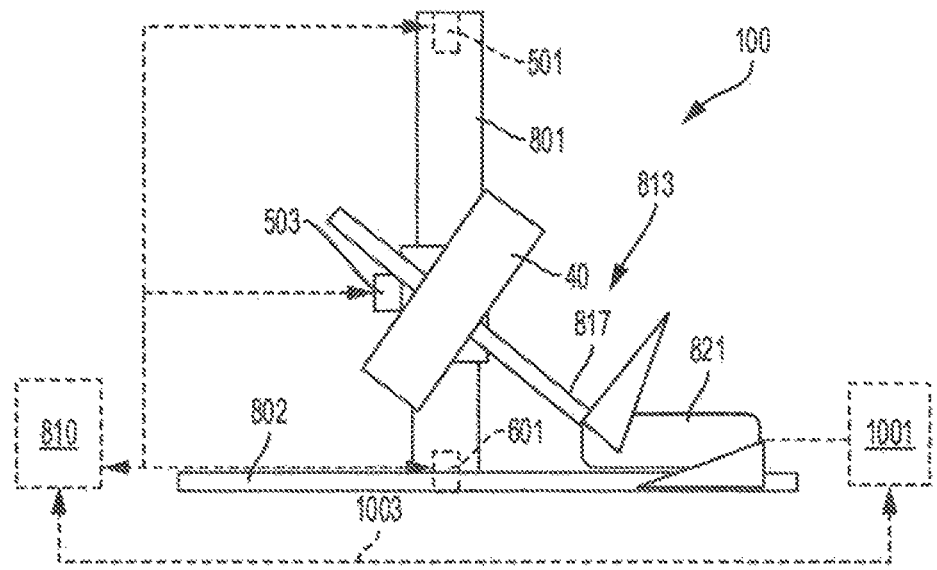

When the patient support 813 is moved to a desired tilt angle, the control system 1001 of the patient support 813 may send a signal to the control system 810 of the imaging system 100 indicating that the system is ready to perform a scan. The control system of the imaging system 100 may send control signals to the first and third drive mechanisms 501 and 601 to perform a coordinated vertical and horizontal translation of the gantry 40 and perform a scan along a tilted axis, as shown in FIG. 10G. In some embodiments, the patient support 813 may be prohibited from moving until the scan is complete.

Figure 10H:
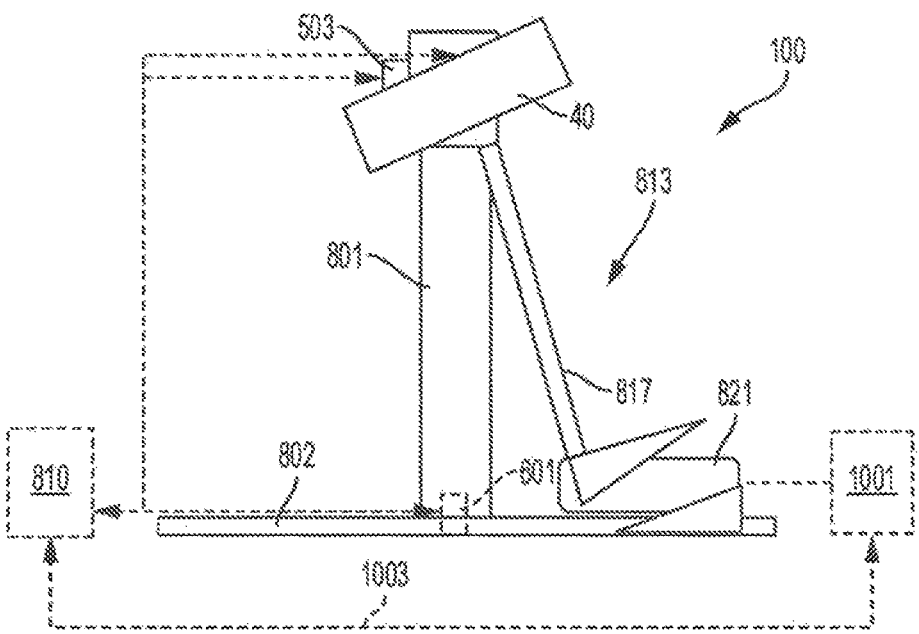
Figure 10I:
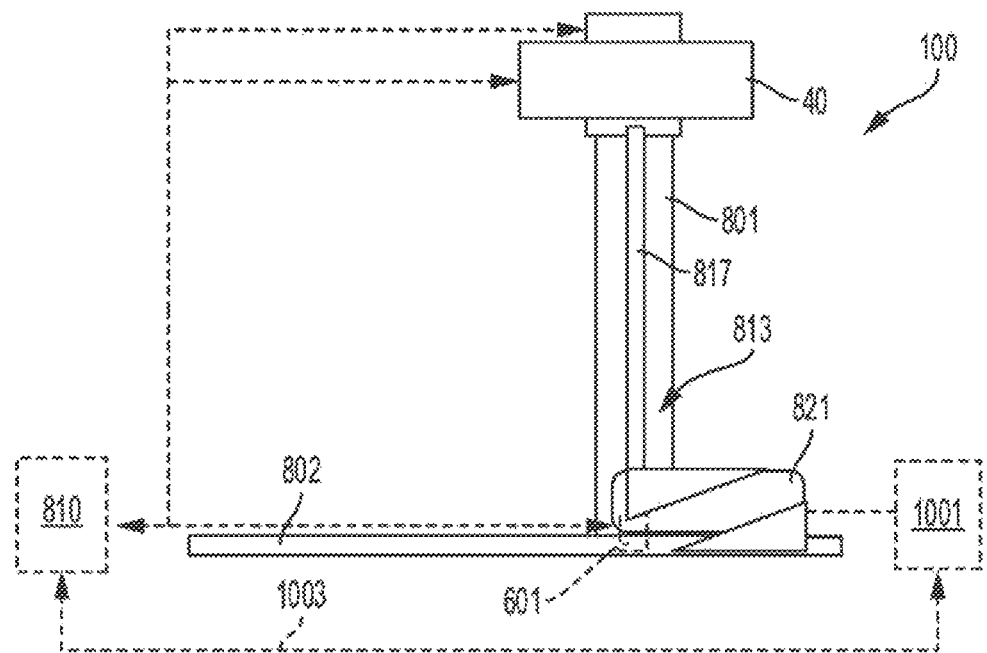

To perform a scan in a vertical direction such as shown in FIGS. 2A-2C, the patient support 813 may be pivoted upwards as shown in FIGS. 10H and 10I. In response to the movement of the patient support 813, the control system 810 of the imaging system 100 may control the first, second and third drive mechanisms 501, 503, 601 to perform a coordinated motion of the gantry 40 as shown in FIGS. 10H and 10I. In particular, the second drive mechanism 503 may rotate the gantry 40 relative to the support column 801 to maintain the bore axis of the gantry 40 aligned with the tilt angle of the patient support 813. The first and third drive mechanisms 501 and 601 may translate the gantry 40 in both a vertical and horizontal direction to maintain the bore of the gantry 40 in alignment with the tip end of the patient support 813. The gantry 40 may maintain a pre-determined separation distance from the tip end of the patient support 813 as follows the motion of the patient support 813. In some embodiments, gantry 40 may move to maintain the outer face of the gantry 40 separated from the tip end of the of the second portion 817 of the patient support 813. Alternately, the gantry 40 may move to maintain the tip end of the second portion 817 at least partially inside the bore of the gantry 40.

Figure 10J:
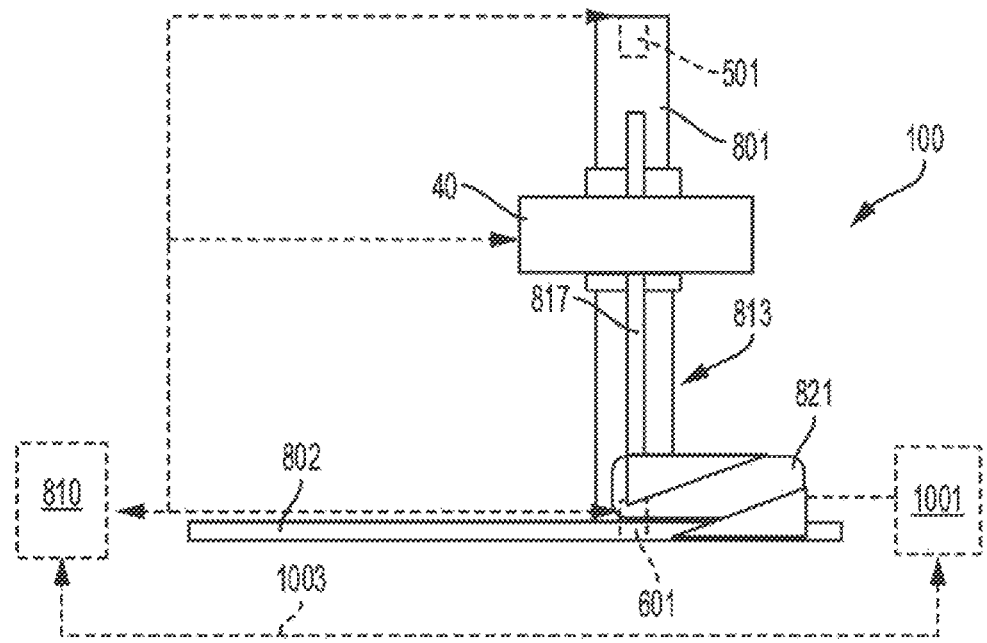

When the patient support 813 is moved to vertical orientation as shown in FIG. 10I, the control system 1001 of the patient support 813 may send a signal to the control system 810 of the imaging system 100 indicating that the system is ready to perform a vertical scan. The control system of the imaging system 100 may send control signals to the first drive mechanism 501 to translate the gantry 40 down the length of the patient support 801 to perform a vertical scan of the patient, as shown in FIG. 10J. In some embodiments, the patient support 813 may be prohibited from moving until the scan is complete.

Figure 10K:
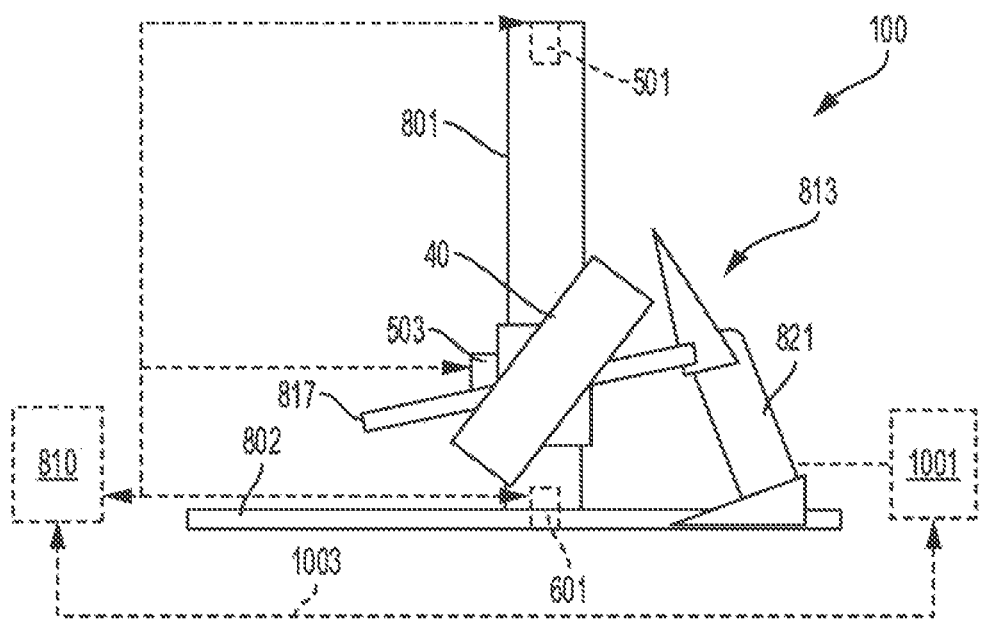

In some embodiments, the patient support 813 may be moved to any arbitrary angle, and may enable the patient to be supported in Trendelenburg and/or reverse Trendelenburg positions. FIG. 10K shows the patient support 813 tilted down from a horizontal position to support a patient in a Trendelenburg configuration. The gantry 40 may be tilted on the support column 801 in the opposite direction from the patient support 813, as shown in FIG. 10K. This may enable imaging of the patient through a variety of different anatomic planes, including, for example, a generally coronal plane (e.g., within ~30° of the coronal plane) through at least a portion of the patient's anatomy. This may be useful, for example, for ENT CT scans of the sinus and/or ears. Also, in brachytherapy, the patient support 813 and gantry 40 may be tilted to a configuration to enable scanning of the prostate region without needing to scan through the patient's femur.

Figure 11A:
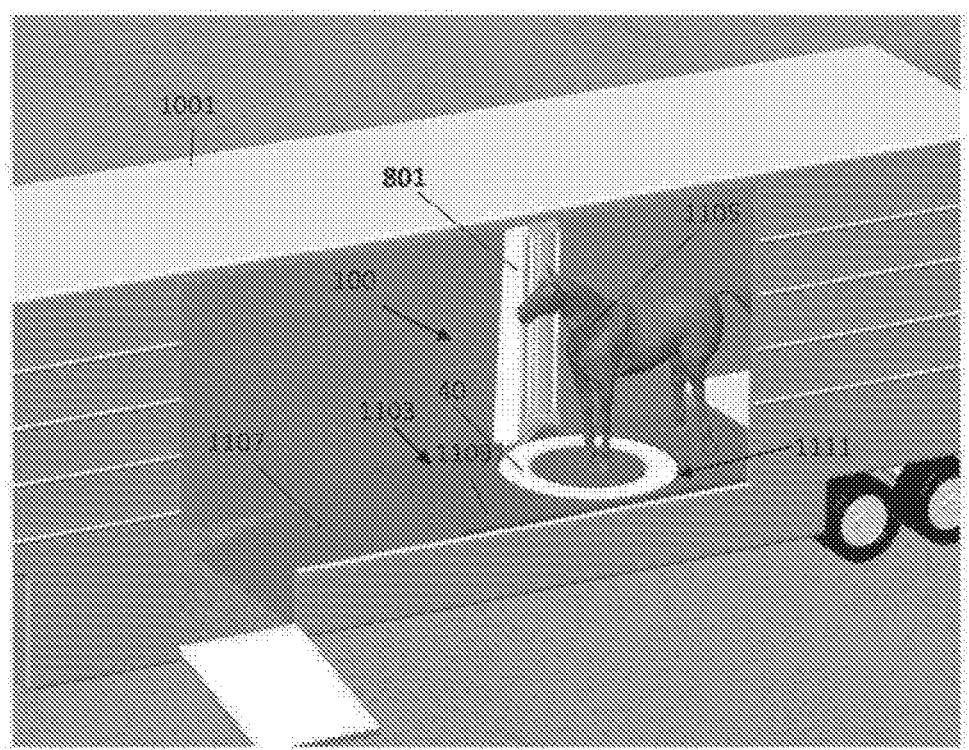
FIGS. 11A-11C illustrate a multi-axis imaging system for imaging an animal in a standing position.
Figure 11B:
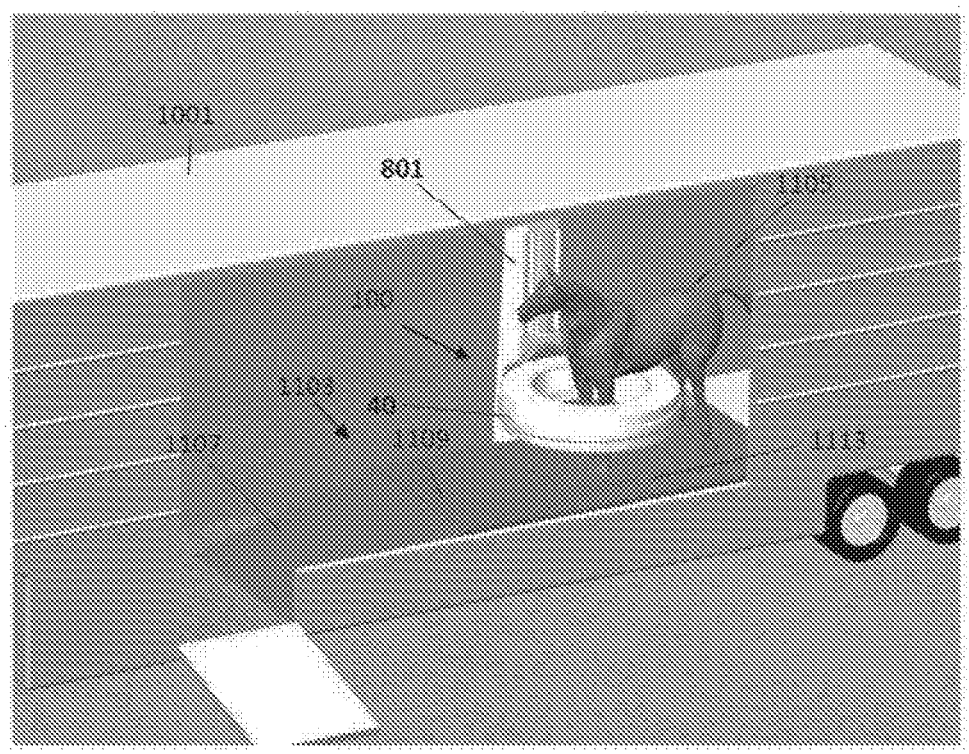
Figure 11C:
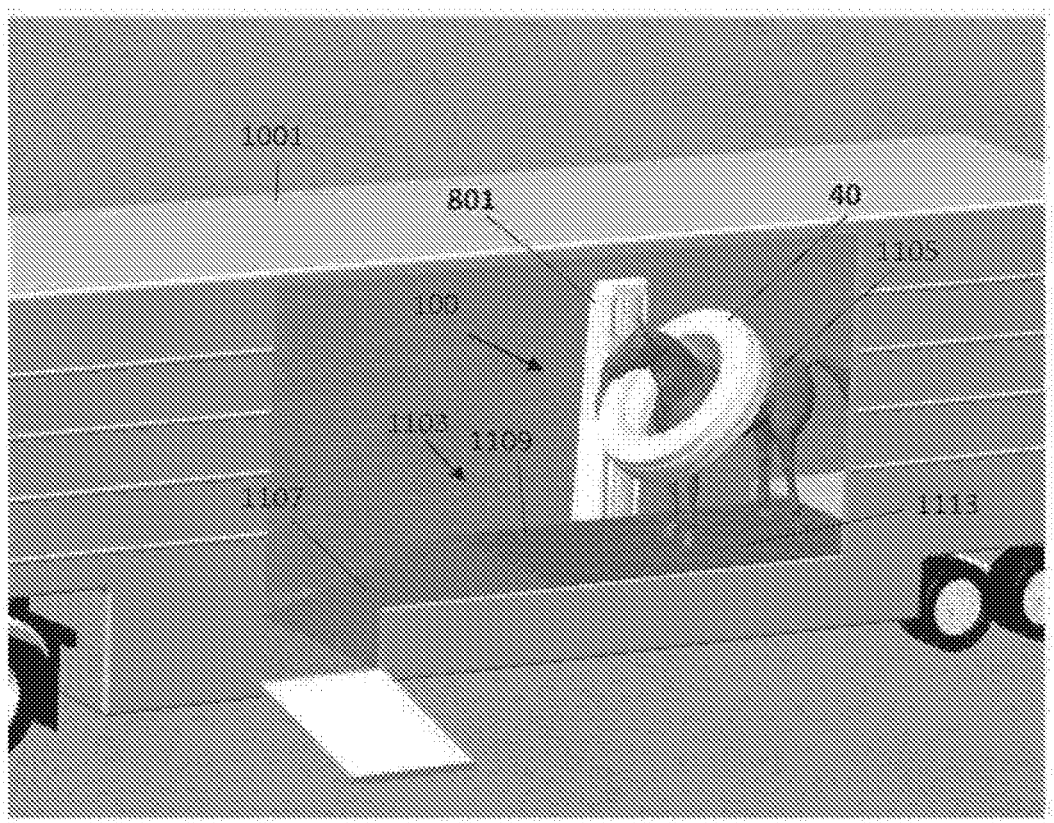

Further embodiments include a multi-axis imaging system 100 that may be utilized for veterinary medicine. A multi-axis imaging system 100 may be used to perform imaging scans of animals, including large animals (e.g., livestock) and/or equine species, in a weight-bearing standing position. An example of the system 100 is shown in FIGS. 11A-11C. The system 100 in this embodiment is located on a mobile trailer 1101. However, it will be understood that the system 100 may be a fixed system located in a veterinary hospital/clinic, or another location such as a farm, ranch or zoo. The system 100 includes an imaging gantry 40 attached to a support column 801 in a cantilevered manner, as described above. The gantry 40 may be rotatable with respect to the support column 801 and may also translate along the length of the support column 801 in a vertical direction. Although not visible in FIGS. 11A-11C, the system 100 may also include a base 802 that supports the support column 801 and gantry 40, and the support column 802 and gantry 40 may be translatable with respect to the base 802 in a horizontal direction. The system 100 may further include a support stage 1103. An animal 1105, such as a horse as shown in FIGS. 11A-11C, may be positioned on the top surface 1109 of the support stage 1103. One or more ramp portions 1107 may enable the animal 1105 to easily climb up and down from the top surface 1109. A cavity 1111 may be provided in the support stage 1103 for housing the gantry 40, as shown in FIG. 11A. The cavity 1111 may have a shape that corresponds with the shape of the gantry 40. When the gantry 40 is lowered into the cavity 1111, the outer side wall of the gantry 40 may be flush with the top surface 1109.

The gantry 40 may be raised up from the cavity 1111 to perform a vertical scan of the legs of the animal 1105 standing on the support stage 1103, as shown in FIG. 11B. An actuator system may optionally raise the bottom surface 1113 of the cavity 1111 up even with the top surface 1109 of the support stage 1103 in coordination with the raising of the gantry 40. This may prevent the animal 1105 from accidentally stepping into the cavity 1111. Following the scan, the gantry 40 may be lowered back into the cavity 1111, and the animal 1105 may climb down from the support stage 1103.

FIG. 11C illustrates the multi-axis imaging system 100 performing a scan of the neck of a standing animal 1105. The gantry 40 is raised out of the cavity 1111 and positioned such that the neck of the animal 1105 is located within the bore of the gantry. A control system for the imaging system 100 may control the system to perform a coordinated vertical translation of the gantry 40 along the support column 801 and a horizontal translation of the gantry 40 and support column 801 along the base 802 to scan along the neck of the animal 1105.

Various examples of diagnostic imaging applications that may be performed on a human or animal patient in a weight-bearing position using an embodiment multi-axis imaging system 100 include, without limitation:

Imaging the bones of a foot. The three-dimensional relationships of the bones in the foot in a flatfoot deformity are difficult to assess with standard radiographs. CT scans demonstrate these relationships but are typically made in a non-weightbearing mode. The use of a weightbearing CT or other imaging apparatus may be useful in imaging the feet in patients with severe flexible pesplanus deformities and to better define the anatomical changes that occur.

Imaging of a limb (e.g. leg). Weight-bearing (CT) bilateral long leg hip to ankle examination and non-weight bearing cross-sectional imaging (CT) of the affected limb may be performed on the hip, knee and ankle, for example, and may be useful for determining variations in angulation and alignment accuracy for diagnosis and/or surgical planning.

Imaging of a spine. Weight bearing scanning (e.g., CT scanning) may be useful for improvements in the accurate diagnosis of degenerative spinal disorders by scanning a patient in the "real life" standing position. By scanning in the standing position, the spinal disc and facet joint compresses, which may enable more specific and precise diagnosis of degenerative spine disorders.

Imaging of a joint (e.g., knee). Weight bearing scanning (e.g., CT scanning) of the knee may enable more specific and precise diagnosis of the patella-femoral kinematics and may also be useful in surgical planning.

Angiography. Weight bearing angiography (e.g., CT angiography) may enable more accurate diagnosis, and may be used, for example, to examine the pulmonary arteries in the lungs to rule out pulmonary embolism, a serious but treatable condition. Weight bearing angiography may also be used to visualize blood flow in the renal arteries (those supplying the kidneys) in patients with high blood pressure and those suspected of having kidney disorders. Narrowing (stenosis) of a renal artery is a cause of high blood pressure (hypertension) in some patients and can be corrected. A special computerized method of viewing the images makes renal CT angiography a very accurate examination. This is also done in prospective kidney donors. Weight bearing angiography may also be used to identify aneurysms in the aorta or in other major blood vessels. Aneurysms are diseased areas of a weakened blood vessel wall that bulges out—like a bulge in a tire. Aneurysms are life-threatening because they can rupture. Weight bearing angiography may also be used to identify dissection in the aorta or its major branches. Dissection means that the layers of the artery wall peel away from each other—like the layers of an onion. Dissection can cause pain and can be life-threatening. Weight bearing angiography may also be used to identify a small aneurysm or arteriovenous malformation inside the brain that can be life-threatening. Weight bearing angiography may also be used to detect atherosclerotic disease that has narrowed the arteries to the legs.

Figure 12:
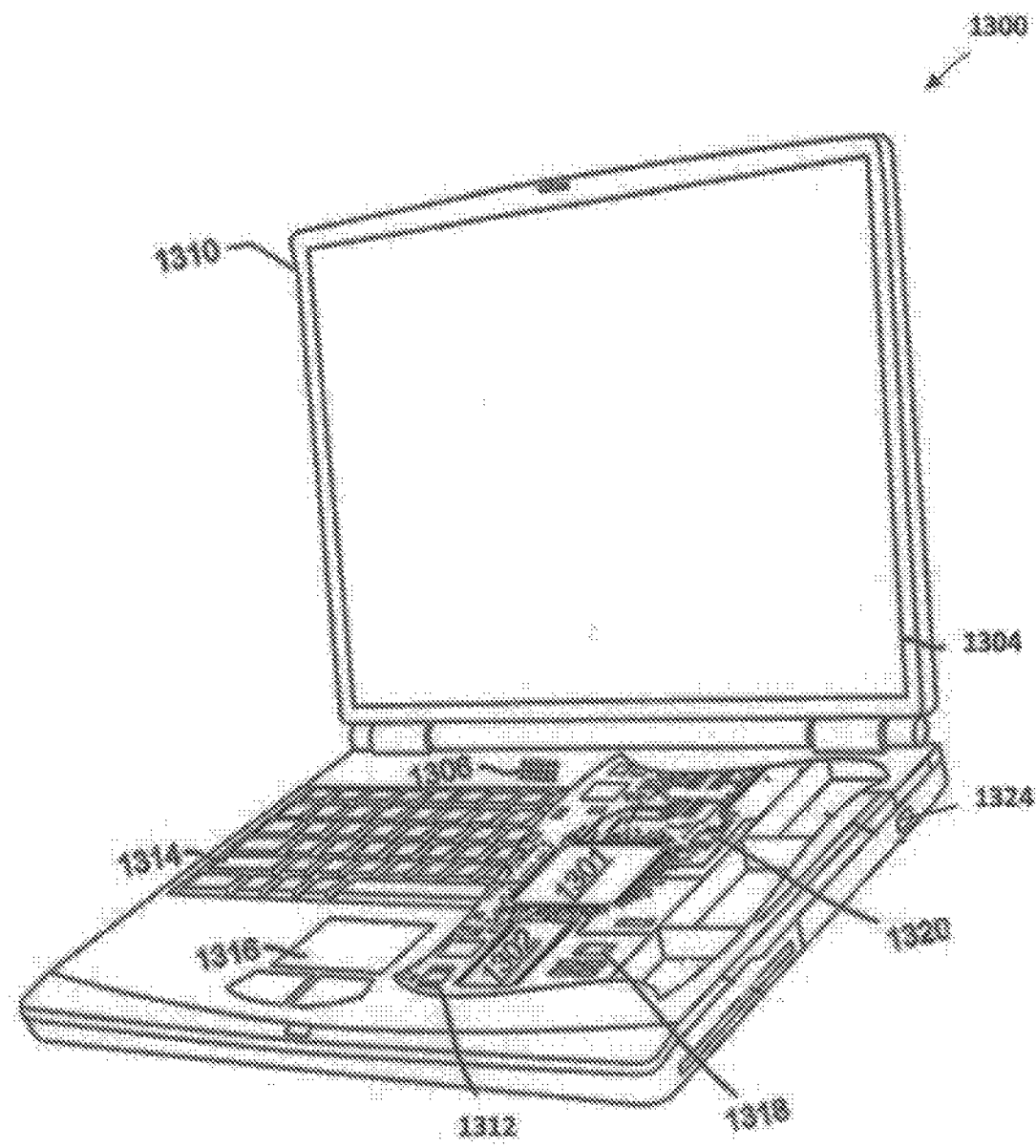
FIG. 12 schematically illustrates a computing device which may be used for performing various embodiments.

FIG. 12 is a system block diagram of a computing device 1300 useful for performing and implementing the various embodiments described above. The computing device 1300 may perform the functions of a control system 810 for a multi-axis imaging system 100 and/or a control system 1001 for a patient support 813, for example. While the computing device 1300 is illustrated as a laptop computer, a computing device providing the functional capabilities of the computer device 1300 may be implemented as a workstation computer, an embedded computer, a desktop computer, a server computer or a handheld computer (e.g., tablet, a smartphone, etc.). A typical computing device 1300 may include a processor 1301 coupled to an electronic display 1304, a speaker 1306 and a memory 1302, which may be a volatile memory as well as a nonvolatile memory (e.g., a disk drive). When implemented as a laptop computer or desktop computer, the computing device 1300 may also include a floppy disc drive, compact disc (CD) or DVD disc drive coupled to the processor 1301. The computing device 1300 may include an antenna 1310, a multimedia receiver 1312, a transceiver 1318 and/or communications circuitry coupled to the processor 1301 for sending and receiving electromagnetic radiation, connecting to a wireless data link, and receiving data. Additionally, the computing device 1300 may include network access ports 1324 coupled to the processor 1301 for establishing data connections with a network (e.g., LAN coupled to a service provider network, etc.). A laptop computer or desktop computer 1300 typically also includes a keyboard 1314 and a mouse pad 1316 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A multi-axis imaging system, comprising:
   an imaging gantry with an imaging axis extending through a bore of the imaging gantry;
   a support column that supports the imaging gantry on one side of the gantry in a cantilevered manner;
   a base that supports the imaging gantry and the support column;
   a first drive mechanism that translates the gantry in a vertical direction relative to the support column and the base;
   a second drive mechanism that rotates the gantry with respect to the support column between a first orientation where the imaging axis of the imaging gantry extends in a vertical direction parallel to the support column and a second orientation where the imaging axis of the gantry extends in a horizontal direction parallel with the base; and
   a third drive mechanism that translates the support column and the gantry in a horizontal direction along the base;
   wherein the first drive mechanism comprises a non-backdrivable drive system including a motor geared into a lead screw that extends along a length of the support column, and a carriage connected with the gantry has a nut fixed thereto that engages with the lead screw such that a rotation of the lead screw drives a translation of the carriage and the gantry in a vertical direction relative to the support column, the lead screw and the nut are free from backdriving under load.

2. The multi-axis imaging system of claim 1, wherein the support column comprises a plurality of rails extending parallel to one another over a surface of the support column and the gantry is mounted to the carriage having bearing elements that engage with the rails to displace the gantry in a vertical direction relative to the support column.

3. The multi-axis imaging system of claim 2, wherein the first drive mechanism comprises a motor geared into a threaded shaft that extends along the length of the support column, and the carriage has a nut fixed thereto that engages with the threaded shaft such that a rotation of the threaded shaft drives a translation of the carriage and the gantry in a vertical direction relative to the support column.

4. The multi-axis imaging system of claim 3, wherein the second drive mechanism is mounted to the carriage.

5. The multi-axis imaging system of claim 4, wherein the second drive mechanism comprises a motor mechanically coupled to a first race of a rotary bearing such that the motor drives the rotation of the first race relative to a second race of the rotary bearing, and the first race is attached to the gantry and the second race is attached to the carriage.

6. The multi-axis imaging system of claim 5, wherein the motor drives a drive wheel that engages with a drive belt that extends over a surface of the first race and drives the rotation of the first race relative to the second race.

7. The multi-axis imaging system of claim 6, wherein opposing ends of the drive belt are attached to the first race.

8. The multi-axis imaging system of claim 1, wherein the base comprises at least one rail extending along a length of the base, and the support column is mounted to a platform having at least one bearing element that engages with the at least one rail to displace the support column and the gantry in a horizontal direction with respect to the base.

9. The multi-axis imaging system of claim 8, wherein the third drive mechanism comprises a drive belt extending along the length of the base parallel to the at least one rail and a motor mounted to the platform that drives a drive wheel that engages with the drive belt to drive the displacement of the support column and the gantry.

10. The multi-axis imaging system of claim 9, wherein the base comprises at least one cover attached to the platform and/or the support column that extends from and retracts into a housing based on the translation of the support column relative to the base.

11. The multi-axis imaging system of claim 1, wherein the gantry comprises:
    a shell forming a circumferential wall and at least one side wall of the gantry;
    a rotor having one or more imaging components mounted to the shell that rotates within a housing defined at least partially by the shell; and
    a bearing assembly that includes a first race, a second race and a bearing element between the first race and the second race that enables the first race and the second race to rotate concentrically relative to one another, the first race is attached to the shell and the second race is attached to the rotor.

12. The multi-axis imaging system of claim 11, wherein the bearing assembly is attached to the shell of the gantry to accommodate a limited amount of bending or deflection of the shell between a first end of the gantry that is attached to the support column and a second end of the gantry opposite the first end while maintaining the relative rotation of the first and second races of the bearing assembly within a plane.

13. The multi-axis imaging system of claim 11, wherein the first race is attached to the shell in a plurality of attachment locations such that the bearing assembly is suspended from the shell when the gantry is rotated to the first orientation.

14. The multi-axis imaging system of claim 13, wherein the first race is not attached to the shell at a distal end of the bearing assembly opposite the first end of the gantry.

15. The multi-axis imaging system of claim 13, wherein the first race is attached to the shell at a first pair of attachment locations along a first secant line of the gantry that is parallel to a midline of the gantry extending between the first and second ends of the gantry and at a second pair of attachment locations along a second secant line of the gantry that is parallel to the midline of the gantry, and the first secant line and the second secant line are equidistant from the midline of the gantry.

16. The multi-axis imaging system of claim 15, wherein the attachment locations located proximate to the second end of the gantry include a plate located between a bottom surface of the shell and a top surface of the first race that provides a gap between the shell and the bearing assembly, and a fastener extending through the shell and an opening in the plate and into the first race of the bearing assembly.

17. The multi-axis imaging system of claim 16, wherein the plate is attached to a bottom surface of the shell and includes a slot having a length extending along the direction of gantry deflection, and a bushing located within the slot and having a length dimension that is less than the length dimension of the slot and an opening through which the fastener is inserted.

18. A method of operating a multi-axis imaging system comprising a moveable imaging gantry including attached to a support column that supports the imaging gantry on one side of the gantry in a cantilevered manner, a base that supports the imaging gantry and the support column, a first drive mechanism that translates the gantry in a vertical direction relative to the support column and the base, a second drive mechanism that rotates the gantry with respect to the support column; and a third drive mechanism that translates the support column and the gantry in a horizontal direction along the base, the method comprising:

receiving, from a control system of a moveable patient support, data indicating a position and a tilt angle of the patient support; and sending control signals to one or more drive systems of the multi-axis imaging system to cause the gantry to translate and/or rotate to maintain the gantry spaced away from the patient support and a bore of the gantry aligned with the patient support in response to the data received from the control system of the moveable patient support wherein the gantry is moveable by translating in a first direction and in a second direction and by rotating with respect to an axis extending in a third direction, where the first, second and third directions are mutually orthogonal;

wherein the gantry is spaced away from the patient support by a distance sufficient to prevent a surface of the gantry from colliding with the patient support or a patient supported thereon while the patient support is moving; and wherein the first drive mechanism comprises a non-backdrivable drive system including a motor geared into a lead screw that extends along a length of the support column, and a carriage connected with the gantry has a nut fixed thereto that engages with the lead screw such that a rotation of the lead screw drives a translation of the carriage and the gantry in a vertical direction relative to the support column, the lead screw and the nut are free from backdriving under load.

* * * * *